(12) United States Patent
Beaulieu et al.

(10) Patent No.: US 7,294,501 B2
(45) Date of Patent: Nov. 13, 2007

(54) GELDANAMYCIN-PRODUCING STRAINS, USES THEREOF AND METHODS OF PRODUCING SAME

(75) Inventors: Carole Beaulieu, Rock Forest (CA); Julie Beauséjour, St-Étienne de Lauzon (CA); Sonya Agbessi, Montréal (CA)

(73) Assignee: Universite De Sherbrooke, Sherbrooke (CA)

( * ) Notice: Subject to any disclaimer, the term of this patent is extended or adjusted under 35 U.S.C. 154(b) by 77 days.

(21) Appl. No.: 10/728,876

(22) Filed: Dec. 8, 2003

(65) Prior Publication Data

US 2007/0237755 A1    Oct. 11, 2007

(51) Int. Cl.
*C12P 1/20*    (2006.01)
*A12N 63/00*   (2006.01)

(52) U.S. Cl. .............................. 435/253.4; 424/93.43; 435/178

(58) Field of Classification Search ...................... None
See application file for complete search history.

(56) References Cited

U.S. PATENT DOCUMENTS 6,280,719 B1 *   8/2001   Suh .......................... 424/93.43

OTHER PUBLICATIONS

Beausejour et al., Abstracts, The Canadian Phytopathological Soc. annual meeting, London, Ontario, 2001. Can. J. Plant Pathol., vol. 23, p. 194.*
S. Agbessi et al., (2003) Antagonistic properties of two recombinant strains of *Streptomyces melanosporofaciens* obtained by intraspecific protoplast fusion; Appl. Microbiol Biotechnol 62:233-238.
K. Bouchek-Mechiche et al. (2000) Differences in host range, pathogenicity to potato cultivars and response to soil temperature among *Streptomyces* species causing common and netted scab France; Plant Pathology 49: 3-10.
Ryszard Brzezinski et al., (1997) Actinomycetes as model organsims for the study of chitosanases; European Chitin Society ISBN 88-86889-01-1: 291-295.
N. Côté et al., (2001) Suppressive effect of chitin waste-based composts on common scab of potato; Chitin Enzymology ISBN 88-86889-06-02:155-161.
R.G. Cuero et al. (1991) Aflatoxin control in preharvest maize : effects of chitosan and two microbial agents; Journal of Agricultural Science, Cambridge, 117 : 165-169.
C. DeBoer et al. (1970) Geldanamycin, A new antibiotic; The Journal of antibiotics Sep. 1970: 442-447.
Cyr Lézin Doumbou et al. (1998) Selection and Characterization of Microorganisms Utilizing Thaxtomin A, a Phytotoxin Produced by *Streptomyces scabies;* Applied and Environmental Microbiology, Nov. 1998 vol. 64, No. 11: 4313-4316.
Cyr Lézin Doumbou et al. (2002) Actinomycetes, promising tools to control plant diseases and to promote plant growth; Phytoprotection 82 : 85-102.

Cyr Lézin Doumbou et al. (2001) Taxonomix Study on Nonpatrogenic *Streptomycetes* Isolated from Common Scab Lesions on Potato Tubers; System. Appl. Microbiol. 24: 1-6.
EC Eckwall et al. (1997) Isolation and characterization of an antibiotic produced by the scab desease-suppressive *Streptomyces diastatochromogenes* strain PonSSII; Journal of Industrial Microbiology & Biotechnology 19: 220-225.
Esther Faucher et al. (1992) Characterization of actinomycetes isolated from common scab lesions on potato tubers; Canadian journal of Plant Patology; 14 : 197-202.
Tamo Fukamizo et al. (1997) Chitosanase from *Streptomyces* sp. Strain N174: a comparative review of its structure and function; Biochem. Cell Biol. 75: 687-696.
C. Goyer et al. (1996) Taxonomic studies on *Streptomycetes* causing potato common scab: a review; Canadian journal of Plant Pathology vol. 18(2): 107-201.
C. Goyer et al. (1998) Pathogenicity of *Streptomyces scabies* Mutants Altered in Thaxtomin A Production; Phytopathology Publication No. P-1998-0316-02R 442-445.
Shinsaku Hayashida et al. (1989) Control of Potato Common Scab with an Antibiotic Biofertilizer Produced from Swine Peces Containing *Streptomyces albidoflavus* CH-33; Agric. Biol. Chem., 53(2): 349-354.
Shigehiro Hirano et al. (1989) Effects of Chitosan, Pectic Acid, Lysozyme, and Chitinase on the Growth of Several Phytopathogens; Agric. Biol. Che., 53(11) 3065-3066.
Cinthia Labrie et al. (2001) Effect of chitin waste-based composts produced by two-phase composting on two oomycete plant pathogens; Plant and Soil 235: 27-34.
D.H. Lambert et al. (1989) *Streptomyces scabies* sp. Nov., nom. Rev.; International Journal of Systematic Bacteriology, Oct. 1989: 387-392.
Daqun Liu et al. (1995) Biological Control of Potato Scab in the Field with Antagonistic *Streptomyces scabies;* The American Phytopathological Society vol. 85, No. 7: 827-831.
J.M. Lorang et al. (1994) Identification of Potato Scab Inducing and Suppressive Species of Streptomyces; The American Phytopathological Society vol. 85, No. 3: 261-268.
Craig S.Rothrock et al. (1984) Role of antibiosis in antagonism of *Streptomyces hygroscopicus* var. geldanus to Rhizoctonia solani in soil; Can. J. Microbiol. 30: 1440-1447.
A.D. Ryan et al. (1997) Inoculum Density and Population Dynamics of Suppressive and Pathogenic *Streptomyces* Strains and Their Relationship to Biological Control of Potato Scab; Biological Control 10: 180-186.
Tony Savard et al. (2002) Antimicrobial Action of Hydrolyzed Chitosan against Spoilage Yeasts and Lactic Acid Bacteria of Fermented Vegetables; Journal of Food Protection, vol. 65, No. 5: 828-833.

(Continued)

*Primary Examiner*—Irene Marx
(74) *Attorney, Agent, or Firm*—Goudreau Gage Dubuc

(57) ABSTRACT

A use of an inoculum of a geldanamycin-producing strain able to survive in a plant rhizosphere as a biocontrol of common scab affecting the plant and a method for biocontrolling common scab comprising the use of such strain. A biologically pure culture of a *Streptomyces* strain deposited at the American Type Culture Collection (ATCC) Accession number BAA-668, or a variant thereof.

6 Claims, 11 Drawing Sheets

OTHER PUBLICATIONS

Vicky Tousaint et al. (1997) Characterization of actinomycetes antagonistic to Phytophthora fragariae var. rubi, the causal agent of raspberry root rot; Phytoprotection 78(2): 43-51.

S.R. Trejo-Estrada et al. (1998) In vitro and in vivo antagonism of *Streptomyces violaceusniger* YCED9 against fungal pathogens of turfgrass; World Journal of Microbiology & Biotechnology, vol. 14: 865-872.

Diane Valois et al. (1996) Glucanolytic Actinomycetes Antagonistic to Phytophthora fragariae var. rubi, the Causal Agent of Raspberry Root Rot; Applied and Environmental Microbiology, vol. 62, No. 5: 1630-1635.

* cited by examiner

```
GGTCTCGAGGGCCCGGCC GTG ACC ATC GAC ACC GCC TGC TCG TCG TCG CTG GTG GCG            40
CTG CAC CTT GCC GCG CAG GCG CTG CGG CAG GGT GAA TGC TCG CTG GCG CTG GCG            94
GGC GGG GTG GCC GTG ATG TCC ACC CCC GGC ACC TTC GTG GAG TTC AGC CGT CAG           148
CGG GGT CTT GCG CCG GAC GGC CGG TGC AAG GCG TTC GCG GCG GCA GCG GAC GGT           202
ACG GGC TGG GGC GAG GGT GTG GGC ATG CTG CTG CTG GAG CGG CTG TCG GAC GCG           256
CGG CGC AAC GGA CAC CAG ATC CTC GCG GTG GTA CGC GGC TCC GCC GTC AAC CAG           310
GAC GGT GCG AGC AAC GGG CTC ACC GCG GCC CAA TGG CCC TCG CAA CAG CGG GTG           364
ATC CGG GCG GCG CTG GCC AAC GCG CGG CTG TCG GCG GCC GAG GTG GAC GTG GTC           418
GAG GCG CAT GGT ACG GGT ACC ACG CTG GGC GAC CCG ATC GAG GCG CAG GCG CTT           472
CTT GCC ACG TAC GGC CGT GAA CAC ACC GAC GAC CAG CCC CTG TGG CTC GGC TCG           526
ATC AAG TCC AAC ATC GGG CAC ACC CAG GCC GCG GCC GGT GTC GCG GGC ATT ATG           580
AAG ATG GTG CTT GCC ATG CGG CAT GGT CTG TTG CCG CAG ACG CTG GGC GTC GAC           634
GAA CCG TCG CCG CAC ATC GAC TGG ACG GCG GGA GCC TCG AAG CTG CTC ACC GAG           688
GCC AGG GCC TGG CCC GAG ACC GAC CGC CCA CGG CGG GCG GGC GTC TCG TCC TTC           742
GGC CTC AGC GGC ACC  AAC GGC CAC ATC ATT CTC GAA CAG GAG CCG CCG ACC GAG          796
GCC GAC GAG GAA ACC  TCC CAG GAG GAC GCG CAA CTT CCT CCC GCC GTC GTG CCA          850
TGG GTG CTG TCG GCG  AAG TCC GAT GCC GGT GTG CGG GGG CAG GCC GCG CGA CTG          904
CAG TCG GCG GTG GCC  GGG GAT ACC AGC CCG GGG ATG ACG GAC ATC GGT CTG TCG          958
CTG GTC ACC ACG CGT  GCG GCG TTC GAG CGG CGG GCG GTG GTA CTG GGT GGT GAC         1012
CGT GCC GCG CTC GTC  AGT GGC CTG ACC GCG CTG ACC GAG GGC CGG GAG GCG ACG         1066
CGC GTG GTG CGG GGG GCC GTG GTC GGC TCC GAT GCC CGA GTG GCC TTT GTC TTT         1120
CCT GGT CGA GGG GTC GCA GTG GGT GGG GAT GGC GGC TGG GTT GCT GGA GTC TTC         1174
GCC GGT GTT CGC GGA GCG ATT GGT GAG TGT GCG GCG GCT TCG GCG CCG TTC GTC         1228
GAC TGG TCG CTC GGG GAT GTG TTG CGG GGT GGG AAG GGT GCT GCG GAG GCG TTG         1282
GAG CGG GTG GAT GTG GTG CAG CCG GTG TTG TGG GCG GTG ATG GTG TCG TTG GCG         1336
GAG CTG TGG CGT TCG TAC GGT GTG GAG CCT GCG GCC GTT ATC GGT CAT TCG CAG         1390
GGT GAG ATC GCG GCG GCG TGT GTG GCG GGT GCG TTG TCG CTG GAG GAC GCC GCG         1444
```

Figure 6

```
CGC GTG GTG GCG TTG CGA AGC CAA GCA CTG CGG GCG TTG TCC GGC GGT GGT GGC            1498
ATG GTG TCG GTA TCA CTG CCC GTG AAG GCG GTA CGA GAG CGG CTG GTC CGG TGG            1552
GGT GAG CGG CTG TCG GTG GCA GCG GTG AAC GGG CCC TCG GCG GTT GTT GTC TCG            1606
GGT GAC GCG GAC GCG TTG GAC GAG CTG CTG GCG GTG TGC GAG GGC GAG GAG ATC            1660
CGG GCC CGT CGC ATC CCC GTG GAC TAC GCC TCG CAC TGC GCC CAT GTG GAG GAA            1714
ATC GAG GAG ACG TTG TTG CGG GAG CTG GCG GAT ATC GCT CCC CGG GCG TCG TCG            1768
GTG CCG TTC TAC TCC AGG GTC ACG GCA GGC GTG CTC GAT ACG ACC GGA CTG GAC            1822
GCC GGG TAC TGG TAC CGG AAT CTG CGT CAG ACG GTC CGC TTC GAT GAG ACC GTA            1876
CGC ACC CTC CTG GCC GAC GGC TTC CAG GTG TTC ATC GAG GCC AGC GCC CAC CCC            1930
GTC CTG ACG ATG GGA GTG GAG CAG ACG GCC GAG GAC CAC GGC ACC CGC GTC ACC            1984
GCC GTC GGT TCC CTG CGC CGC GAC GAT GGC GGT CCC GAC CGG TTC GCC ACC TCC            2038
CTC GCC GAG GCG TAT GTC GGC GGC GCG CCC GTC GAC TGG GCG AGG ATG TTC GCC            2092
GGA ACG GGC GCG GAG CGG GCC GAT CTG CCG ACG TAT GCC TTC CAG CGC ACG CAC            2146
TTC TGG CTG GAG TCC GAG ACG GTC GAG GCC GGT GAT GTG CCG TCG GTG GGG CTG            2200
GAC TCG GCC GGG CAT CCG TTG CTG GGT GCC GCC GTG CCG CTG CCC GAC TCC GAC            2254
GGC TTC CTG CTC ACC GGC CGG CTG TCG CTC CGT ACC CAT CCC TGG GTC GCC GAC            2308
CAC GCG GTG GCG GAT GTA ACG CTG CTG CCC GGG ACG GCC TTC GTG GAG CTG CTG            2362
ATG CGG GCC GGT GAC GCG GTC GGC TGC GAC CGG GTG GAC GAA CTG ACC CTG GGA            2416
GCA CCG CTT GTG CTG CCC GAG CAG GGC ACG GTC CGG CTG CAG GTC GCC GTC GGC            2470
GGC CCC GAC GAG GCG GGG CGG CGC TCG GTC GGT GTG TAC GCG CAG ACG GAG GAC            2524
GGC CCC TGG ACG CAG CAC GCG ACC GGT GTG CTC GGC GGC GGT GTG CTC GGC GGC            2578
GGC AGC AGC TCG GCC GAT CGC GTC ACT GAG ACG GAG GCA TGG CCA CCG ACT GGT            2632
GCG GAG GCC GTT GAT GTC GCC GGG CTC TAC GAG AGG TTC GCC CGG ACC GGA                2683
```

Figure 6 (continued)

```
   1  TACCCGGGTG  GCGCTGGCCT  TCGTCAGTXG  CTATCTCTTC  GGGCGCGGCC
  51  ACAGGGGGAC  CTTGGTCCTC  GGCCTCGCGG  TCTCGCCGCG  GGCAAGCGGC
 101  TCTCCGGTAT  CAGCCCACCG  GGCGCCCAGG  CACTGAAGTC  CTCCGAGCTC
 151  GGCAAGCTGG  GCCAGGAGAT  CGGCAGCCGG  CTGGTCTCCG  CGGGTCGGGA
 201  GGCGGCCATG  TCGGCGGCCA  GTAGCCGCAT  CGACGGCCTG  AGCGACCCGC
 251  TGGAGCACCG  CGCCACGGCG  CTGCGCACCG  GCGGCGCGGG  GGGCGGGGAG
 301  CCGGAGSCGG  GGAGGACGAG  GAGCCGGACG  AGCAGGAGGA  GCGCGAGCCA
 351  CGCGAGCCCA  CCGGCAAGCA  GCAGCRCAAG  CCGGCCGACC  GTXCGGCGCA
 401  GGCCAGGAAG  CGGACGGYTC  CXAAGGgCTC  GCGCGACGXA  GCCAGAXGTG
 451  AGGGCCATGG  CTGAGGAAAC  CCCCAAGGGG  CGGGCCSGTG  GGCGCSGCGC
 501  CTGCCCACCG  ACCACCTGXC  GAAGXAAGCA  CAGGGCCTGC  TGATGGCGCT
 551  GGSCGAAAAG  GCTCTGGAAT  CGGTCACCCA  CCTGGGGGGC  AACCCCGGGA
 601  CGGGCGCGCT  XAAGGGCGGA  CTGGACCAGG  TCAAGGGCAA  GGTCGTCGAC
 651  ACGGCCAAGG  AGCAGATCAA  GGAGAAGGTC  AAGGACCAGG  TCAAGGAAAA
 701  GGTCGTCGAC  AAGGCCAAGA  GCTTCATCCC  GGGCCTCGGC  GGTGGCGGCG
 751  ACGGTGGCGG  CAAGGGCGGC  AAGAAGCTCA  AGGTCACCAA  CATCGTGGAG
 801  CAGATCGACG  TGGGCGCGCC  CCTCTCCCTC  ACCTACAACC  TCTGGACGGA
 851  GTGGGAGAAC  TTCCCCTCGT  ACATGAAGAA  GGTCGAGGAC  GTCCAGAACC
 901  AGGGCGAGGA  GGAGGGTGAG  GACGAGGACG  GGHCCGGGAC  GGAATCCGAG
 951  TGGAAGGCCC  AGGTCTTCTG  GTCGCACCGC  AAGTGGCAGG  CAGAGGTCGT
1001  CGAGCAGGTG  CCCGAACAAG  SCGGATCATC  TGGAGCGTCT  VCgGGCCGAD
1051  CAAGGGMCCA  TGTSCGACRG  VACGATCACC  TTCCATGAGC  TGGCCCCCGA
1101  GCTCACCCGG  ATCC
```

Figure 7

```
   1  GCATGCGSGC GGGCGGCGAA SSGcGTTCGT CGGTCACGGG GGCGTAGGCG
  51  TAGGCCCSGC CACGCGGGGT GCGGGTGAGC AACTGCTTGG TGTGCATACG
 101  GGTGAGGATC GTCACCACGC TGTTGTAGGC CAGTTCGCCG CCGAGGCGTT
 151  CGGTGACCTC CCGGGGGGTC AGCGCGCCGT CGGCCCGCTG CAGCAGTTCG
 201  AGGATCTCGG CCTCGCGGGC ACCGTTGGGC CGCTTGGGCC CGTGTCCTGG
 251  CGTGCGGATG CCCATGCGGT TGGCCTCCCT CATCTCATCA CCCBACACTC
 301  GTGTAGGACT CCTACACCGG TGTAAAAGCT GTTGTCTCCC AAGTGTGCCA
 351  TGCACGCGTG CCTGGGCAGA ACTCTGCCTT GGGCGGGCAC GGSCGGAAAG
 401  GACCCTGCGG TGCCTTTGGC CCTCAACCCG CTGGATGCCG CCGAACTGCT
 451  GACAGCGTTC GGCACGGCGG GTGTCTTCGT GGTGCTGTTC GCCGAGACCG
 501  GACTTCTGAT CGGCTTCTTC CTGCCCGGTG ACTCCCTGTT GGTCACCGCC
 551  GGCCTKCTGT GTACGGCCTC GGGCAGGGGC GTCCACCTGT CGGTGCCCGG
 601  TGTGCCGGTC CGTACCCGCG GCCGGCACCT GATCGACGGT GTTAGGCGTG
 651  CGGAGGAGCT TCTYGgCCGV TACGACCGCT ACCGGTTCCT CTGTTCGCGC
 701  TGATCGACGC GTYTYCCCGC TGCCGCTCGC CCTGGGAGCG CTCAGGTCCC
 751  GCCGGGCCCG CaCCGCCGSG GAGCCGACCG TGGGGAGCGC CAAGTGAaGA
 801  CACCTTCCCC TGATCCACAA CGTGTACGCG ATCGGCGGVA CGATCCGCAC
 851  CAAGCTAAAT CTCGCCGCCG GGCTCGCCGA CCGGCACRAG GTGACGAYCG
 901  TATCGATGCT CCGCCACCGC ACCXACCCGC GAtTCCGTCA TCGATCCACG
 951  GGTGACGGTC GTGCCCCTGG TTGACATACA CGCgGACGCC GCCGACCCCC
1001  TGCTGCATCA GCCGGCCGAG GTCTTCCCCA CCGCCGAGAA GCGGTACAGG
1051  CAGTACAGCC GCCTCACCGA CCAGSGGGCG CGCGAGTACC TGCgGAAGCT
1101  GCGACGCGGA CGTGATCATC GGCACGCGGC CGGGCATCAA TGTGTACCTG
1151  GCCCCTTCGC ACCGCCCCGG gCACTGCGCA TCGCCCAGGA ACACCTCACC
1201  CACGASACGC ACACCAAGAG CTGCGCGCCC AGCTCGSSSG CCAGTACCGC
1251  GACCTGGATG CCGTGGTCAC CACGACCGAA GCCGACGCGG CCGTCTACCG
1301  GGCGAGATGC GGCTGCCGGG CGGGgG
```

Figure 8

MTTSTSSPAASSASPARQVVVGLAERSYTVHIGHGVQRLLPQVVAALGARRAVVVTARPAEQTPDPGVPSLVVPA
RDGEAAKDLAAVTDLCRRFVGFGLTRSDVVVSCGGGTTTDTVGLAAALYHRGTPVVHVPTSLLAQVDASVGGKTA
VNLPEGKNLVGAYWQPAAVLCDLEHLKTLPEREWRNGLGEIARCHFIGAPDLDGLPLLDQISASVTLKAGIVAAD
ERDSGLRHLLNYGHTLGHALERATGFALRHGEGVAIGTVFAGRLAGALGRIGPERVAEHHDVVARYGLPTALPPH
VSVSELVELMRLDKKATDGLTFVLDSPAGPGLVRGIAEDTVGATLAAMPRAPAW

Figure 9

```
62558      ca ccatgcgggc gcgcggggca
62581 tcgccgcgag ggtggcgccg acggtgtcct cggcgatccc gcgcaccagt ccgggccccg
62641 cggggctatc caggacgaac gtcagcccgt cggtggcctt cttgtccagg cgcatcagct
62701 ccaccagctc ggacacggag acatgcgggg gcagcgcggt cggcaggccg tagcgggcga
62761 ccacgtcatg atgctcggcc acgcgctccg ggccgatgcg ccccagcgcg ccggcgagcc
62821 ggccggcgaa aaccgtgccg atggccactc cctccccgtg ccgcagcgcg aacccggtgg
62881 cacgttccag cgcatgcccc aacgtgtgtc cgtagttgag gaggtggcgc aggcccgagt
62941 cgcgctcgtc cgcggcgacg atgcccgcct tgagcgtcac actggccgag atctggtcga
63001 gcagcggcag cccgtcgaga tcgggcgcgc cgatgaagtg gcagcgggcg atctcaccga
63061 ggccgttgcg ccattccgt tcgggcaggg tcttcagatg ttcgaggtcg cagagcacgg
63121 ccgcgggctg ccagtaggcg ccgaccagat tcttgccctc gggcagattc accgcggtct
63181 tcccgccgac gctcgcgtcc acctgggcga gcagcgaggt cggcacgtgt acgaccgggg
63241 tgccccggtg gtagagggcg cggccaggc ccaccgtgtc ggtcgtggtg ccgccgccac
63301 aggacaccac cacatccgag cgggtcagtc gaatccgac gaaccggcgg cacagatcgg
63361 tcacggcggc caggtccttg gccgcctccc cgtcgcgggc gggtacgacg agcgagggca
63421 ctcctgggtc ggggtctgc tcggcgggcc gcgcggtgac caccaccgcc ctgcgcgcgc
63481 ccagggcggc caccacctgt gggagcagcc gctgcacacc gtgtccgatg tgcacggtgt
63541 aggagcgttc ggccagcccg acgacgacct gtcgggcggg ggaagcggaa ctggcggccg
63601 gactggaagt cgacgtggtc aa
```

Figure 10

MDKRTMGRHRRITQPPRTTLATRAVLAAGVLVPTIASAGSAHAATPQAAICTSDRPELADKLSEDINSALEGSAA
TTAISLHDRTTNTTCTLDADRHFDSASTVKVTVLSTLLWDAQKDNRALTQEEKDHATAMITESDNDATTALWKQL
GADKINGFLQAAGMTNTTLDSEGHWGLTQITANDEEKLLQLVTHTNPVLSDDSRAYILKLTAEVIPSQRWGTPAG
APSDAQVHVKNGWLERATNGWRVHSLGAFTGGDHDYTITVLSQDNATMDDGIANIEGIARAVHENLNAPVSSAQS

Figure 11

```
 771 ttacgactga
 781 gcgctggaca cgggcgcgtt gaggttctcg tggaccgcgc gggcgatgcc ctcgatgttg
 841 gcgatgccgt cgtccatcgt ggcgttgtcc tgcgagagca ccgtgatcgt gtagtcgtgg
 901 tcgccgccgg tgaaggcgcc gaggctgtgc acccgccagc cgttcgtggc ccgctccagc
 961 cagccgttct tcacatgcac ctgggcgtcg ctcggcgcgc cggccggggt gccccagcgc
1021 tgcgagggga tgacctcggc cgtcagcttc aggatgtagg cgcgggagtc atcgctgagc
1081 accgggttgg tgtgggtcac cagttggagg agctttcct catcgttcgc ggtgatctgg
1141 gtgagccccc agtggccctc gctgtcgagg gtggtgttgg tcattcccgc ggcctgcagg
1201 aaccgttga tcttgtccgc cccgagctgc ttccacagcg cggtggtggc gtcgttgtcg
1261 gactctgtga tcatggcggt ggcatggtcc ttctcctcct gtgtcagggc gcgattgtcc
1321 ttctgcgcgt cccacagcag ggtgctgagc acggtcacct tgaccgtgct cgcggagtcg
1381 aagtgccggt ccgcatccag agtgcaggtg gtgttcgtgg tgcggtcgtg gaggctgatc
1441 gccgtggtgg cggcggagcc ctccagcgcc gaattgatgt cctcggagag cttgtcggcg
1501 agttccggcc ggtccgaggt gcagatcgcc gcctgcgggg tggccgcgtg agccgacccc
1561 gccgaggcga tcgtcggcac gagcaccccg gcggccagca ccgctcttgt cgccagggtg
1621 gtacggggag gctgggttat tcgtcggtgt cgacccatgg tgcgcttgtc cat
```

GELDANAMYCIN-PRODUCING STRAINS, USES THEREOF AND METHODS OF PRODUCING SAME

FIELD OF THE INVENTION

The present invention relates to geldanamycin-producing strains, uses thereof and methods of producing same. More specifically, the present invention is concerned with these strains and uses thereof as biocontrol agents against common scab.

BACKGROUND OF THE INVENTION

Common scab is a disease widely distributed in potato-growing areas. Superficial or deep corky lesions on potato tubers characterise the disease. *Streptomyces scabies* (Lambert and Loria, 1989) is the main causal agent of the disease (Goyer et al., 1996). Methods used to control common scab include chemical treatments of seed potato tubers (Davis et al., 1976), irrigation (Adams and Lapwood, 1978), soil amendments (Weinhold and Brown, 1968), cultivar choice (Bouchek-Mechiche et al., 2000) and rotation strategies (Li et al., 1999).

Biological control of potato scab by nonpathogenic streptomycetes was also reported (Doumbou et al., 2001b; Doumbou et al., 1998; Liu et al., 1995a; Ryan and Kinkel, 1997). For example, introduction into an infested soil of some *Streptomyces* diastatochromogenes and *S. albogriseolus* strains isolated from suppressive soils decreased common scab symptoms on potato tubers (Eckwall and Schottel, 1997; Liu et al., 1995a; Lorang et al., 1995). Common scab severity was also decreased by an amendment of an antibiotic biofertilizer produced from swine feces containing *S. albidoflavus* strain CH-33 (Hayashida et al., 1989). These strains are not known to produce geldanamycin.

Geldanamycin is known to inhibit the growth of several plant pathogenic fungi (Toussaint et al., 1997) and geldanamycin-producing streptomycetes were shown to protect crops against several fungal diseases (Rothrock and Gottlieb, 1984; Valois et al., 1996). This antibiotic is also active against some Gram-positive bacteria (Toussaint et al., 1997) such as S. scabies (Agbessi, 2002) but the efficiency of this bioagent to control common scab has not yet been determined. It cannot be predicted whether a strain known to be antagonistic against a microbiological pathogen will be able to compete in the rhizosphere against this pathogen and against other soil microbiological pathogens. It cannot therefore be predicted whether this strain would be effective in controlling a plant disease caused by this microbiological pathogen.

Certain references have shown that specific chitin waste-based composts suppress common scab (Côté et al., 2001; Vruggink (1970)). It was never demonstrated however whether the little amount of chitosan contained in these wastes participated in controlling the disease. Some success of biocontrol have been reported by the combined use of a biocontrol agent and of chitosan without however demonstrating the role played by chitosan itself (Cuero et al., 1991; Singh et al., 1999). Chitosan is known to be toxic against most microorganisms. There thus remains a need to demonstrate whether chitosan may help control common scab and whether it may be used in combination with microorganisms antagonistic to common scab.

There thus remains a need for new effective biocontrols of common scab.

SUMMARY OF THE INVENTION

The present invention demonstrates for the first time the biocontrol efficiency of geldanamycin-producing strains against a bacterial plant disease and more particularly against common scab.

More specifically, in accordance with the present invention, there is provided a use of an inoculum of a geldanamycin-producing strain able to survive in a plant rhizosphere as a biocontrol of common scab affecting the plant. In a specific embodiment, the strain encodes a protein having the sequence of SEQ ID NO: 6 or a homologous sequence having geldanamycin activity. In an other embodiment, the strain comprises the nucleotide sequence of SEQ ID NO: 7 or a homologous sequence having geldanamycin activity. In an other embodiment, the strain comprises a nucleotide sequence able to hybridize under high stringency conditions to the complementary sequence of a sequence selected from the group consisting of: the nucleotide sequence of SEQ ID NO: 1, the nucleotide sequence of SEQ ID NO: 2, the nucleotide sequence of SEQ ID NO: 3, the nucleotide sequence of SEQ ID NO: 5, and the nucleotide sequence of SEQ ID NO: 7. According to specific embodiments, the strain is a *Streptomyces* strain. In more specific embodiments, the strain is selected from the group consisting of *Streptomyces violaceusniger*, *Streptomyces hygroscopicus* and *Streptomyces melanosporafasciens* strains. In more specific embodiments, the strain is deposited at the American Type Culture Collection (ATCC) under Accession number BAA-668. According to specific embodiment, the biocontrol comprises a reduction of the severity of common scab or a reduction of the incidence of common scab.

According to an other aspect of the invention, there is provided a biologically pure culture of a *Streptomyces* strain deposited at the American Type Culture Collection (ATCC) Accession number BAA-668, or a variant thereof. This strain is a *Streptomyces melanosporofasciens* and was deposited at the American Type Culture Collection (ATCC) at P.O. Box 1549 Manassas, Va. 20108 USA under Accession number BAA-668 on Dec. 9, 2002.

According to an other aspect of the invention, there is provided a composition comprising an inoculum of a *Streptomyces* strain deposited at the American Type Culture Collection (ATCC) Accession number BAA-668 and a carrier. In a specific embodiment, the carrier comprises chitosan.

According to an other aspect of the invention, there is provided a method of biocontrolling common scab comprising applying on a plant an effective amount of an inoculum of a geldanamycin-producing strain able to survive in the plant rhizosphere. In a specific embodiment, the strain encodes a protein having the sequence of SEQ ID NO: 6 or an homologous sequence having geldanamycin activity. In an other embodiment, the strain comprises the nucleotide sequence of SEQ ID NO: 7 or a homologous sequence having geldanamycin activity. In an other embodiment, the strain comprises a nucleotide sequence able to hybridize under high stringency conditions to the complementary sequence of a sequence selected from the group consisting of: the nucleotide sequence of SEQ ID NO: 1, the nucleotide sequence of SEQ ID NO: 2, the nucleotide sequence of SEQ ID NO: 3, the nucleotide sequence of SEQ ID NO: 5, and the nucleotide sequence of SEQ ID NO: 7. According to specific embodiments, the strain is a *Streptomyces* strain. In more specific embodiments, the strain is selected from the group consisting of *Streptomyces violaceusniger*, *Streptomyces hygroscopicus* and *Streptomyces* melanosporafasciens strains. In more specific embodiments, the strain is deposited at the American Type Culture Collection (ATCC) under Accession number BAA-668. According to specific embodiment, the biocontrol comprises a reduction of the severity of common scab or a reduction of the incidence of common scab.

According to an other aspect of the present invention, there is provided a method for modifying the biocontrol efficiency of a bacterial strain comprising intraspecific protoplasm fusion of the bacterial strain with an other strain having a desirable biocontrol property against common scab.

According to an other aspect of the present invention, there is provided a method for making a biocontrol agent against common scab, which comprises the steps of: obtaining a microbial strain susceptible of producing geldanamycin; contacting the nucleic acids or the proteins of said strain with a ligand specific to geldanamycin or to a nucleic acid encoding geldanamycin; detecting the formation of a complex as an indication of the presence of geldanamycin or of a nucleic acid encoding geldanamycin in the strain, whereby said strain or a geldanamycin-producing part of said strain may be used as a biocontrol agent against common scab. In a specific embodiment, the ligand is a nucleic acid having at least 12 nucleotides in length hybridizing with the nucleic acids having a sequence complementary to a sequence selected from: a) the nucleotide sequence of SEQ ID NO: 1; b) the nucleotide sequence of SEQ ID NO: 2; c) the nucleotide sequence of SEQ ID NO: 3; d) the nucleotide sequence of SEQ ID NO: 5; and the nucleotide sequence of SEQ ID NO: 7. The ligand may also bind to the geldanamycin protein. Such ligand may include an antibody specific to the geldanamycin.

Robinson et al. (1981) showed that it was possible to increase the level of antibiotic production by protoplast fusion. Biosynthesis of new compounds by recombinant strains obtained by intraspecific protoplast fusion (Fujimoto et al. 1990) as well as by interspecific protoplast fusion (Xiufen and Qi 1989) has been previously reported. The present invention also therefore concerns a method for modifying the biocontrol efficiency of a *Streptomyces* strain comprising protoplast fusion. The Applicant was the first to use such method for modifying the biocontrol efficiency of a microorganism.

As used herein, the terminology "geldanamycin-producing strain" refers to any bacterial strain producing geldanamycin including strains naturally found in the nature such as EF-76, *Streptomyces hygroscopicus* var. *geldanus* ATCC 55256, *Streptomyces* violaceusniger YCED9, *Streptomyces hygroscopicus* strain NRRL 3602. It also refers to any synthetic strain producing geldanamycin such as a recombinant strain produced according to means known by persons of ordinary skill in the art and strains obtained from protoplasm fusion including FP-54. These means include methods of cloning genes of a geldanamycin-producing strain into a non-producing strain.

The terminology "geldanamycin-producing strain" also includes strains containing a sequence encoding a protein identified in Rasher et al. "Cloning and characterization of a gene cluster for geldanamycin production in *Streptomyces hygroscopicus*" *Microbiol. Lett.* 218 (2), 223-230 (2003) as a secreted protein (SEQ ID NO: 6). This sequence is also available in NCBI database under no AY179507. It is reasonably predictable that this secreted protein is geldanamycin. The definition therefore also includes strains containing a nucleotide sequence encoding this protein, namely nucleotide sequence (SEQ ID NO: 7). The definition also includes strains producing a protein having this sequence (SEQ ID NO: 6) or an homologous protein having a geldanamycin activity. <<Homologous>> is intended to mean a protein similar or identical to geldanamycin which is produced by a variant *S. melanosporofasciens* strain, another *Streptomyces* species, another microbial species (e.g. fungus or bacteria) of a natural or synthetic origin. Such homologous or corresponding protein shares amino acid and nucleotide sequences susceptible to encode a protein having the same activity profile as geldanamycin. This activity is monitored on sensitive strains like S. scabies. The definition also includes strains containing nucleotide sequences able to hybridize under stringent conditions to a sequence complementary to sequences involved in geldanamycin biosynthesis. For instance, FP-60, a strain shown not to produce geldanamycin does not hybridize to probes Bm27, Bm3 and BS15. This definition also includes strains possessing a gene encoding an amino DHQ synthase. Indeed, EF-76 (data not shown) and *Streptomyces hygroscopicus* strain NRRL 3602 (see NCBI AY179507) possess a gene encoding an amino DHQ involved in geldanamycin biosynthesis.

As used herein, the terms "EF-76" and "*Streptomyces melanosporofasciens*" are used interchangeably.

As used herein, the terminology "biologically pure" strain is intended to mean a strain separated from materials with which it is normally associated in nature. Note that a strain associated with other strains, or with compounds or materials that it is not normally found with in nature, is still defined as "biologically pure." A monoculture of a particular strain is, of course, "biologically pure."

For the methods and uses of the present invention, it is not necessary that the whole broth culture of the strains of the invention be used. Indeed, the present invention encompasses the use of a whole broth culture of a strain of the present invention, spores produced by such strain, dried biomass of the strains and lyophilized strains. As used herein therefore, the terminology "inoculum of a strain" refers to any form or part of the strain of the present invention or a combination thereof that possesses the desired ability to control common scab.

There is also provided a combination of an inoculum of a strain according to the present invention and of a carrier.

In order to achieve good dispersion, adhesion and conservation/stability of compositions within the present invention, it may be advantageous to formulate the whole broth culture or supernatant with components that aid dispersion, adhesion and conservation/stability or even assist in the biocontrol of the plant disease. These components are referred to herein individually or collectively as "carrier". Suitable formulations for this carrier will be known to those skilled in the art (wettable powders, granules and the like, or carriers within which the inoculum can be microencapsulated in a suitable medium and the like, liquids such as aqueous flowables and aqueous suspensions, and emulsifiable concentrates). Other suitable formulations will be known to those skilled in the art. The carrier may include components such as chitosan, vermiculite, compost, talc, milk powder, gel, etc.

Chitosan, a chitin deacetylated derivative, is another product that was shown effective to control several fungal diseases (Benhamou and Theriault, 1992; Sathiyabama and Balasubramanian, 1998). Protection conferred to plants by chitosan depends on both the elicitation of plant defense mechanisms (Kauss et al., 1989; Pearce and Ride, 1982; Walker-Simmons et al., 1983) and the fungicidal property of chitosan oligomers (Allan and Hadwiger, 1979; Hirano and Nagao, 1989). Chitosan is known to exhibit bacteriostatic activity towards Gram-negative and Gram-positive human pathogens (Allan et al., 1984), foodborne pathogens (Wang, 1992) and lactic bacteria (Savard et al., 2002). Chitosan has usually no toxic effect on microorganisms producing chitosanases. Chitosanolytic organisms would benefit from the presence of chitosan in their environment as carbon and nitrogen sources. Chitosanolytic activities have been reported for strains of different bacterial genera including *Streptomyces* (Fukamizo and Brzezinski, 1997).

As used herein, the terms "mutant" and "variant" are used interchangeably. A variant of the EF-76 strain deposited at the ATCC under access no BM-668 may or may not have the same identifying biological characteristics of the EF-76 strain, as long as the variant possesses biocontrol efficiency against common scab. Illustrative examples of suitable methods for preparing variants of the inventive microorganism strain include, but are not limited to: intraspecific protoplast fusion, mutagenesis by irradiation with ultraviolet light or X-rays, or by treatment with a chemical mutagen such as nitrosoguanidine (N-methyl-N'-nitro-N-nitrosoguanidine), methylmethane sulfonate, nitrogen mustard and the like; gene integration techniques, such as those mediated by insertional elements or transposons or by homologous recombination of transforming linear or circular DNA molecules; and transduction mediated by bacteriophages such as P1. These methods are well known in the art and are described, for example, in J. H. Miller, Experiments in Molecular Genetics, Cold Spring Harbor Laboratory Press, Cold Spring Harbor, N.Y. (1972); J. H. Miller, A Short Course in Bacterial Genetics, Cold Spring Harbor Laboratory Press, Cold Spring Harbor, N.Y. (1992); M. Singer and P. Berg, Genes & Genomes, University Science Books, Mill Valley, Calif. (1991); J. Sambrook, E. F. Fritsch and T. Maniatis, Molecular Cloning: A Laboratory Manual, 2d ed., Cold Spring Harbor Laboratory Press, Cold Spring Harbor, N.Y. (1989); P. B. Kaufman et al., Handbook of Molecular and Cellular Methods in Biology and Medicine, CRC Press, Boca Raton, Fla. (1995); Methods in Plant Molecular Biology and Biotechnology, B. R. Glick and J. E. Thompson, eds., CRC Press, Boca Raton, Fla. (1993); and P. F. Smith-Keary, Molecular Genetics of *Escherichia coli*, The Guilford Press, New York, N.Y. (1989).

Variant strains derived from the EF-76 strain using known methods are then preferably selected or screened for biocontrol efficiency against common scab. In a specific embodiment, fusant cells are selected on the basis of their ability to control common scab. Strain FP-54 described herein constitutes a variant as defined herein. It is a strain obtained from the protoplasm fusion of EF-76 and possesses biocontrol efficiency against common scab.

As used herein, the terminology "biocontrol" is meant herein to refer to reduction of severity or reduction of incidence a plant disease.

As used herein, the terminology "biocontrol efficiency" of a strain refers to the strain's ability to ameliorate or stabilize the state of a plant affected by a disease or reverse, slow or delay progression of the plant disease. It may be assessed though a number of parameters including: antibiotic production, decrease of the plant disease severity index, antagonistic activity against a plant pathogen, antibiosis, lysis, phytotoxin degradation and rhizocompetence. When the biocontrol efficiency assessed is that of strains of the present invention against common scab, the parameters used include antagonistic activity against S. scabies, geldanamycin production, disease severity index of common scab, disease incidence of common scab. As used herein, the term "disease incidence" refers to the percentage of tubers or roots displaying visible signs of common scab lesions.

As used herein, the terminology "common scab" is meant to include any *Streptomyces*-induced common scab including those affecting root and tuber food crops such as red and sugar beets, carrots, parsnips, radishes, rutabagas and turnips (Goyer et al. 1997). Geldanamycin was shown to be active against other common scab causing bacterial species including acidiscabies and caviscabies (data not shown).

As used herein, the terminology "severity of common scab" is meant to refer to the scope of common scab symptoms on vegetal tissues. It may be assessed through a number of means including the determination of the extent of the surface of the plant covered by scab lesions.

As used herein, the terminology "effective amount" is meant to refer to an amount sufficient to effect beneficial or desired results. An effective amount can be provided in one or more administrations. In terms of treatment of and protection against common scab, an "effective amount" is an amount sufficient to ameliorate, stabilize, reverse, slow or delay progression of the plant disease state. In specific embodiments, an "effective amount" is an amount sufficient to ameliorate, stabilize, reverse, slow or delay progression of the plant disease state by at least 5% with regard to a non-treated diseased control plant In other specific embodiments, the effective amount may be comprised between about $10^3$ and $10^9$ spores/g of carrier.

According to the methods of the present invention for applying the inoculum of a strain according to the present invention, the inoculum may be applied on various parts of the plant affected by common scab including the tubers and the root and any part thereof. It may be applied at plantation or later during the season.

Other objects, advantages and features of the present invention will become more apparent upon reading of the following non-restrictive description of preferred embodiments thereof, given by way of example only with reference to the accompanying drawings.

The present description refers to a number of documents, the content of which is herein incorporated by reference in their entirety.

BRIEF DESCRIPTION OF THE DRAWINGS

In the appended drawings:

FIG. 6 shows the DNA sequence of probe Kp38 containing type-I polyketide synthase (PKS) genes (SEQ ID NO: 1);

FIG. 7 shows the DNA sequence of probe Bm27 (SEQ ID NO: 2);

FIG. 8 shows the DNA sequence of Bm3 (SEQ ID NO: 3);

FIG. 9 shows the amino acid sequence of the putative aminoDHQ synthase of *Streptomyces hygroscopicus* strain NRRL 3602 (SEQ ID NO: 4);

FIG. 10 shows the DNA sequence encoding the putative aminoDHQ synthase of *Streptomyces hygroscopicus* strain NRRL 3602 (SEQ ID NO: 5);

FIG. 11 shows the amino acid sequence of the putative geldanamycin protein of *Streptomyces hygroscopicus* strain NRRL 3602 (SEQ ID NO: 6); and FIG. 12 shows the DNA sequence encoding putative geldanamycin protein of *Streptomyces hygroscopicus* strain NRRL 3602 (SEQ ID NO: 7);

DESCRIPTION OF ILLUSTRATIVE EMBODIMENTS

Example 1

Strains Used

*Streptomyces* scabies strain EF-35 and *S. melanosporofaciens* strain EF-76 were isolated from common scab lesions on potato tubers (Faucher et al., 1992). *Streptomyces melanosporofaciens* EF-76 (Doumbou et al., 2001a), formely *S. hygroscopicus* sbsp. geldanus, was selected after screening for the ability to inhibit *Phytophthora* fragariae growth causing raspberry root rot (Valois et al., 1996). Strain EF-76 produces geldanamycin (Toussaint et al., 1997), a polyketide exhibiting antimicrobial activity (DeBoer et al., 1970).

Example 2

Detection medium for chitosanase activity

Chitosanase detection medium was prepared according to Brzezinski et al. (1997) with the following modifications. The detection medium was prepared by adding successively to a sterile base medium (1.74 g of peptone and 3.6 g of agar in 170 ml of distilled water) 90 mL of chitosan solution, 30 mL of solution A, 10 mL of 0.25 M $K_2HPO_4$ and 1 mL of 5N KOH. Chitosan solution was prepared by dissolving 1 g of chitosan (Sigma-Aldrich, St-Louis, Mo.) in 100 mL of 0.1 N HCl. Solution A consisted of 10 g L-1 $MgSO_4$, 10 g L-1 NaCl, 1 g L-1 $K_2HPO_4$, 100 mg L-1 $FeSO_4$, 100 mg L-1 $CaCl_2$, 66 mg L-1 $MnCl_2$ and 7 mg L-1 $ZnCl_2$. Strains were inoculated on the chitosanase detection medium and incubated at 30° C. for 24-48 h. Chitosanase activity was detected by the formation of a clear zone of degradation around the growing colonies.

Figure 5:
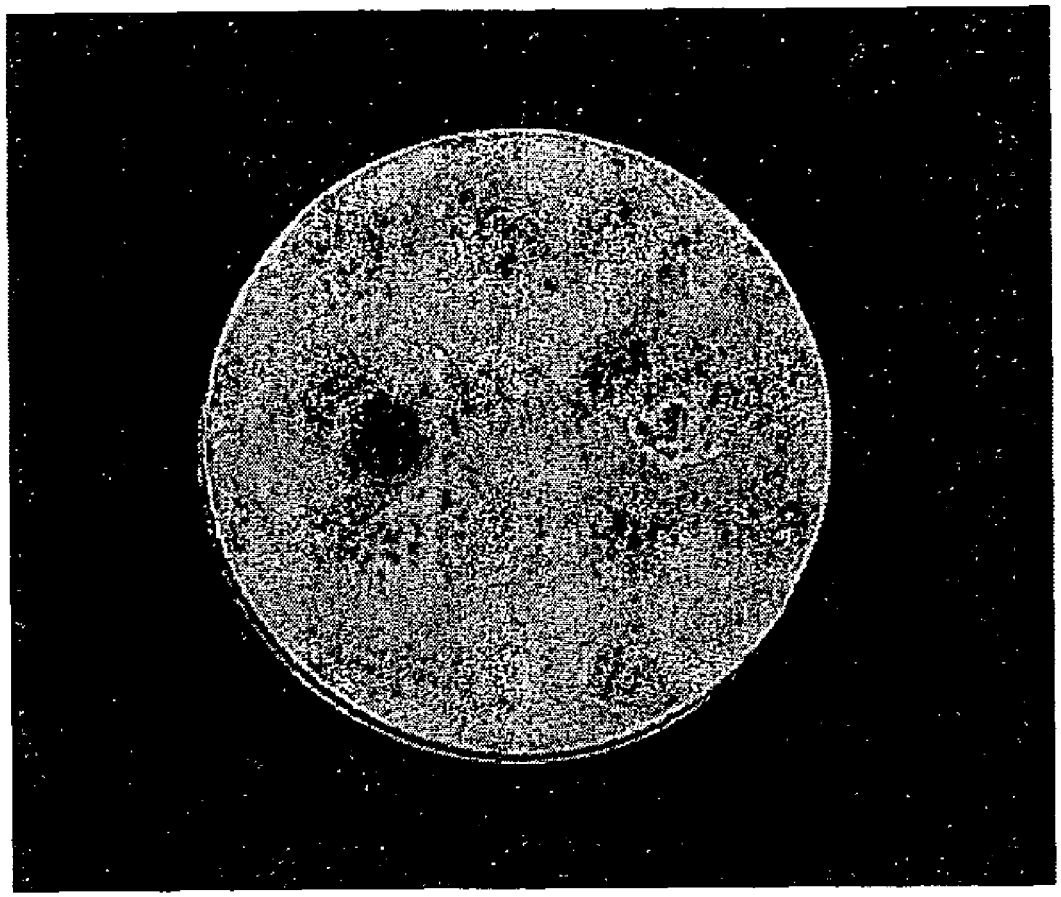
FIG. 5 shows the growth of S. scabies strain EF-35 (left) and of *S. melanosporofaciens* strain EF-76 (right) on a chitosanase detection medium.

FIG. 5 showed that strain EF-76 had the property to hydrolyze chitosan. A clearing zone was observed around EF-76 colony indicating that the insoluble chitosan contained in the growth medium was hydrolyzed. S. scabies strain EF-35 produced melanoid pigment on this medium but no chitosanase activity was detected. Treatments of seed pieces did not appear to affect the yield at harvest. Each year, the yield values of the four treatments did not significantly differ (P<0.05) (Table 2).

Example 3

Greenhouse Assay

The pathogenicity test was carried out using potato tubers (*Solanum tuberosum* cv. Shepody) obtained from glasshouse grown plants derived from tissue culture with no visible sign of disease. Potato tubers were planted in 250-mm diameter pots containing sand and vermiculite (2:1). S. scabies inoculum was prepared as previously described by Faucher et al. (1992). S. scabies strain EF-35 was grown for 2 weeks at 30° C., in 50 mL tubes containing 3 g vermiculite saturated with Say-solution (Labruyere, 1971). This inoculum was mixed with the plant growth substrate before planting. At planting, talc or chitosan (0.5 g) with or without *S. melanosporofaciens* strain EF-76 was sprinkled on the top of each tuber. Spores were previously collected from a 10-day-old culture on YME agar and then mixed with talc or chitosan (108 spores/g of carrier). The pathogenicity test was carried out in five replicates. Pots were randomly dispersed in a greenhouse and their contents were watered every three days. A soluble fertilizer (20-20-20) was added every 2 weeks. The progeny tubers were harvested after three months and were then examined for common scab (Goyer et al., 1998). Disease severity was visually estimated by attributing a disease severity index (1-10) to each tuber in regard of the extent of their surfaces covered with scab lesions. A disease index of 1 was associated to healthy tubers while a disease index of 10 represented tubers covered by scab lesions on more than 90% of their surface.

The highest common scab incidence (43%) was associated with the talc only treatment. When compared to talc only, chitosan only reduced common scab incidence from 43 to 27% but this difference was not statistically different (P<0.05). When progeny tubers were grown in the presence of *S. melanosporofaciens* strain EF-76 independently of the carrier used (talc or chitosan), disease incidence was significantly reduced as compared to that obtained to the talc only treatment and was reduced, although not significantly, as compared to that obtained with the chitosan only treatment (Table 1).

TABLE 1

Effect of chitosan and *S. melanosporofaciens* EF-76 on common scab incidence under controlled conditions

| Treatment | Common scab incidence (%) |
|---|---|
| Talc (control) | 43a[1] |
| Chitosan | 27ab |
| Spores of *S. melanosporofaciens* EF-76 in talc | 11b |
| Spores of *S. melanosporofaciens* EF-76 in chitosan | 14b |

[1]Numbers accompanied by the same letters are not significantly different (P < 0.05, +2 test).

Example 4

Field Assay

Trials were performed in a naturally infested field at L'Assumption (Quebec, Canada) in 2000 and in 2001. At planting, a formulation powder (0.5 g) was added on the top of each tuber (*Solanum tuberosum* cv. Shepody). Formulations consisted of one of two carriers (talc or chitosan) with or without dried biomass of *S. melanosporofaciens* EF-76 (1/300 w:w inoculum/carrier). EF-76 biomass was prepared as follows. The bacteria were grown 7-10 days in a 5 L reactor, in YME liquid medium supplemented with 10 mM $CaCO_3$. The cultures were centrifuged and the pellets were freeze-dried for 18 h. An experimental plot consisted of 4 rows planted with 26 seed tubers. The plots were arranged as randomized complete blocks with 4 replicates. Common scab symptoms were estimated visually on 100 tubers harvested from each plot. The disease incidence as well as the disease severity was scored for each treatment. A disease severity index (1-10) was attributed to each tuber in regard of the extent of their surfaces covered with scab lesions. A disease index of 1 was associated to healthy tubers while a disease index of 10 represented tubers covered by scab lesions on more than 90% of their surface. Yield was determined by the weight (kg) of progeny tubers harvested from each plot.

The four treatments [talc (control treatment), chitosan, talc supplemented with S. melanosporofaciens spores, and chitosan supplemented with S. melanosporofaciens spores] were compared. Treatments of seed pieces did not appear to affect the yield at harvest. Each year, the yield values of the four treatments did not significantly differ (P<0.05) (Table 2).

Common scab was more severe in 2000 than in 2001 as shown by both a higher average disease severity index (an average severity index of 2.43 for 2000 versus 1.43 for 2001) and a higher level of disease incidence (an average disease incidence of 80.3 for 2000 versus 35.8% for 2000) as seen in Table 2.

Each year, the highest common scab disease severity index was associated with the talc only treatment. Common scab severity was significantly lower for all other treatments except for the chitosan treatment in 2001. The level of protection against the disease incidence conferred by chitosan and S. melanosporofaciens spores into talc was equivalent since the disease severity index value for both treatments did not significantly differ in 2000.

If most treatments reduced common scab severity when compared to the talc treatment, only some treatments significantly reduced common scab incidence. In 2000, chitosan with or without S. melanosporofaciens spores reduced the disease incidence of 35 and 8%, respectively. In 2001, S. melanosporofaciens spores in talc or in chitosan reduced the disease incidence of 21 and 23%, respectively. The combination of chitosan and S. melanosporofaciens spores offered in 2000 a protective effect against common scab that was higher than those conferred by chitosan or by S. melanosporofaciens spores in talc. This additive effect was not observed in 2001.

TABLE 2

Effect of chitosan and of S. melanosporofaciens EF-76 on common scab of potato under field conditions

| Treatment | Field assay 2000 | | | Field assay 2001 | | |
|---|---|---|---|---|---|---|
| | Disease severity index | Disease incidence (%) | Yield (kg/plot) | Disease severity index | Disease incidence | Yield (kg/plot) |
| Talc (control) | $2.83a^1$ | $91a^2$ | $53.6a^1$ | $1.61a^1$ | $47a^2$ | $61.9a^1$ |
| Chitosan | 2.36b | 83b | 45.8a | 1.53a | 46a | 60.6a |
| Strain EF-76 in talc | 2.49b | 91a | 49.3a | 1.26b | 26b | 58.8a |
| Strain EF-76 in chitosan | 2.05c | 56c | 49.2a | 1.31b | 24b | 56.6a |

[1]Numbers of the column that are accompanied by a same letter did not significantly differ (P < 0.05, ANOVA test).
[2]Numbers of the column that are accompanied by a same letter did not significantly differ (P < 0.05, ÷2 test).

Effect of a combination of EF-76 and chitosan

EF-76 appears to be an efficient biocontrol agent against common scab of potato. For the two consecutive years in the field trial, this strain, when applied with talc, reduced disease severity as compared to that obtained with to the control treatment. EF-76 also reduced disease incidence in the 2001 field assay but not in 2000. The level of pathogenic inoculum possibly affected the ability of EF-76 to reduce common scab incidence. The disease incidence was reduced when the pathogen inoculum was moderate (the greenhouse assay and the 2001 field trial) but not when the inoculum was high (the 2000 field assay). Inoculation of potato seeds with EF-76 reduced the common scab index both in growth-chamber and field conditions.

The present invention presents the first demonstration of biocontrol by a geldanamycin-producing strain against a bacterial disease.

Effect of a combination of EF-76 and chitosan

Figure 1:
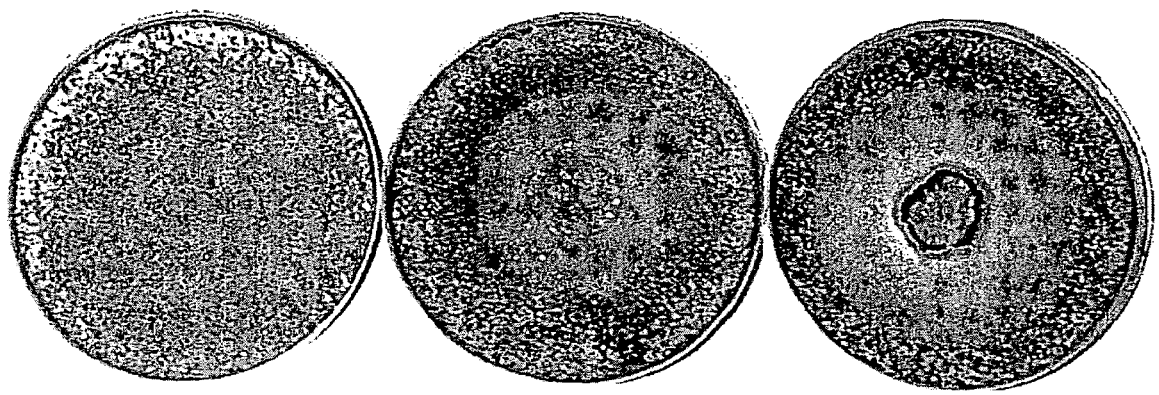
FIG. 1 shows the growth of *Streptomyces* scabies EF-35 in the presence of *Streptomyces melanosporofaciens* strains FP-60 (A), EF-76 (B), and FP-54 (C)

As may be seen in FIG. 1, EF-76 exhibited chitosanolytic activity and thus could be protected against the toxic effect of chitosan.

Combination of chitosan and EF-76 ensured in both controlled and field conditions a significant decrease of disease severity and of disease incidence when compared to the control treatment. Even better, the combined use of strain EF-76 and of chitosan provided in some cases a higher protection than did strain EF-76 in talc or chitosan by itself. Even though this additive effect was not always observed, combined application of chitosan and EF-76 was always one of the best treatments. As the effectiveness of chitosan and of EF-76 in the control of common scab seems to be differentially influenced by environmental conditions such as the level of pathogen inoculum, the combined use of both products would ensure in most conditions a significant level of protection.

Example 5

Intraspecific Protoplastic Fusion of the Wild-Type Strain EF-76

Protoplasts of the strain EF-76 were made according to the procedure described by Hopwood et al. (1985). A solution of 50% PEG 1000 in P buffer (Hopwood et al. 1985) was added to 10⁸ protoplasts. These protoplasts were resuspended and kept 5 min at room temperature. Samples of this suspension were plated on R2YE medium (Hopwood et al. 1985) and incubated at 30° C. After their regeneration on R2YE plates, colonies were streaked on YME medium for the screening of strains improved or deficient in antibiotic production.

Several hundreds colonies were recovered from the protoplast fusion experiment. Among these colonies, 100 were streaked on YME medium and tested for their ability to inhibit the growth of *B. cereus* ATCC 14579. Seven isolates were positively or negatively affected in their inhibition power against *Bacillus* when compared to the wild-type strain EF-76.

Two fusants were studied in more detail, namely FP-54 (ATCC BM-669) and FP-60 (ATCC BM-670).

Prototrophy of FP-54 and FP-60

The nutritional requirements of strains FP-54 and FP-60 was verified by inoculating them on minimal medium [$(NH_4)_2$ $SO_4$ 2 g/l, $K_2HPO_4$ 0.5 µl, $MgSO_4.7H_2O$ 0.2 g/l, $FeSO_4.7H_2O$ 0.01 g/l, glucose 5 g/l and agarose 15 g/l]. Bacterial growth was observed after 5 days of incubation at 30° C. The ability of the two fusant strains to produce b-1,3-glucanase, b-1,4-glucanase and b-1,6-glucanase was tested in the same minimal medium containing, instead of glucose, 0.4% laminarin (Sigma-Aldrich, St. Louis, Mo., USA), 1% carboxymethylcellulose (Fluka, Buchs, Switzerland) and 1% pustulan (Calbiochem, San Diego, Calif., USA), respectively. The plates were incubated 5 days at 30° C. and then overlaid with a solution of Congo red (0.2%) for 10 min followed by two washes with a 1 M NaCl solution. A clear zone appeared around colonies when the carbohydrate had been degraded.

Like the wild-type strain EF-76, strains FP-54 and FP-60 were able to grow on a minimal medium. These strains retained the ability to catabolize laminarin, cellulose, and pustulan. Their growth patterns were different from that of the wild-type strain. At stationary phase, the biomass reached by strains FP-54 and FP-60 was smaller than that of strain EF-76 (data not shown).

Growth curves of EF-76, FP-54 and FP-60

Growth curves of strains EF-76, FP-54 and FP-60 were established as follows. Two-day-old cultures were used after standardisation to inoculate 100 ml of a fresh YME medium. The flasks were incubated at 30° C. Ten-ml samples were then withdrawn periodically and the dry weight of cells recovered from these samples was determined. This experiment was carried out in triplicate.

Southern blot analysis

BamHI-digested genomic DNA was transferred onto Hybond N™ nylon membrane (Amersham Pharmacia Biotech, Baie d'Urfé, Canada). Genomic DNAs were hybridized with four probes (Kp38, Bm27, Bm3, BS15). These probes all came from a contiguous 40-kb DNA fragment of strain EF-76 genome (Agbessi 2002). Probes were labeled with digoxigenin-dUTP using a kit (Roche Molecular Biochemicals, Laval, Canada). The samples were prehybridized (150 min) and hybridized (overnight) at 68° C. After the incubation, the membranes were washed twice in 2×SSC (150 mM NaCl, 15 mM sodium citrate) containing 0.1% SDS for 7 min at 68° C. and twice in 0.1×SSC containing 0.1% SDS for 20 min at 68° C. As used herein, these conditions qualify as "high stringency conditions". Blots were developed with a colorimetric development kit according to manufacturer specifications (Roche Molecular Biochemicals).

Genetic characterization of strains FP-54 and FP-60

The taxonomic identity of two selected fusant strains (FP-54 and FP-60) was determined by partial sequencing of the 16S rRNA gene (Doumbou et al. 2001a).

Strains FP-54 and FP-60 exhibited a 16S rDNA sequence identical to that of strain EF-76 over the 600-bp region sequenced for the three strains. Probes Kp38, Bm27, Bm3 and BS15 were hybridized with the genomic DNA of strains FP-54 and FP-60 to detect genetic modifications.

Figure 2:
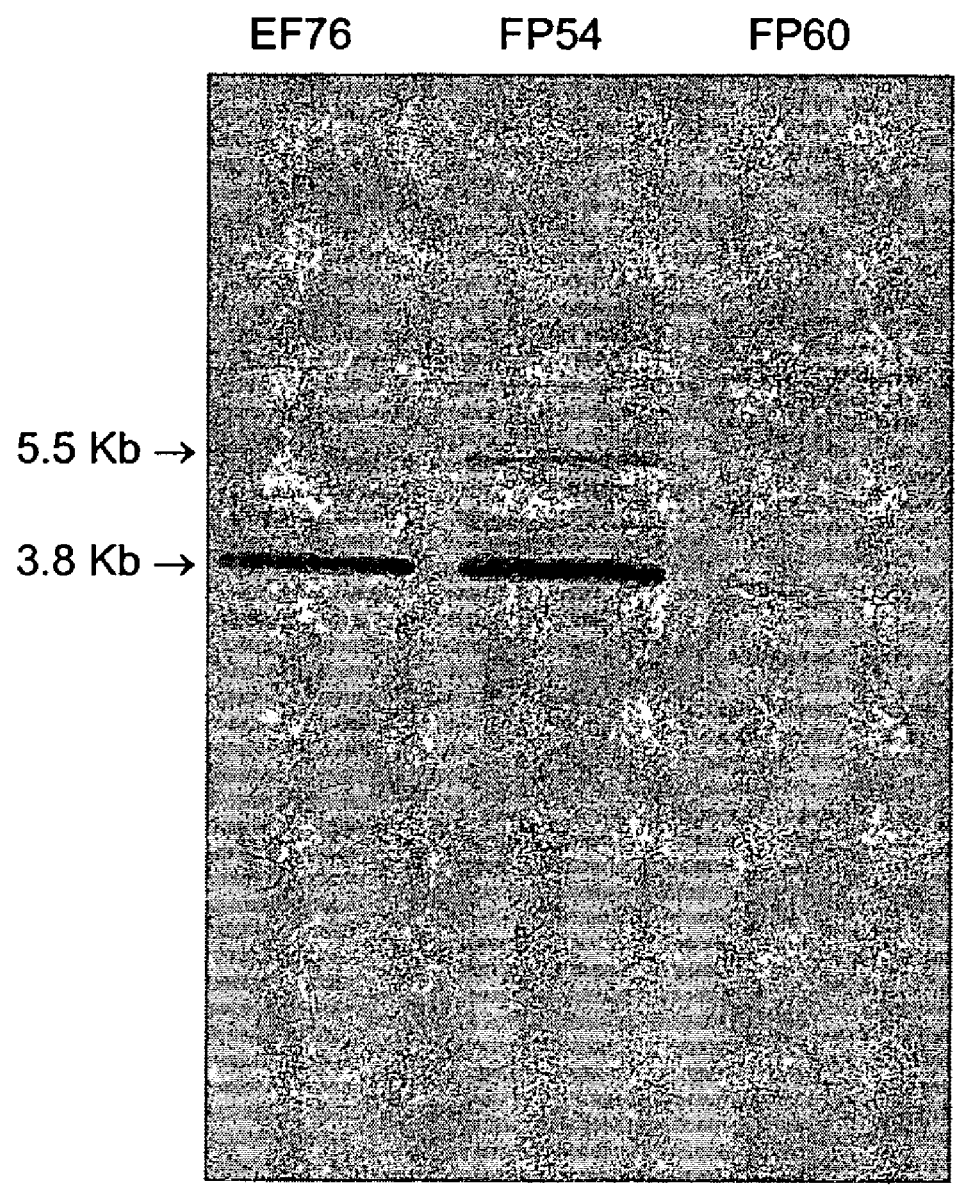
FIG. 2 presents a southern blot hybridization between BamHI-digested genomic DNAs of *S. melanosporofaciens* strains EF-76, FP-54 and FP-60 and probe Kp38 (SEQ ID NO: 1)

FIG. 2 presents the hybridization between BamHI-digested genomic DNAs of *S. melanosporofaciens* strains EF-76, FP-54 and FP-60 and probe Kp38. This probe contains regions of the ketoacylsynthase and acyltransferase domains of type-I polyketide synthase (PKS) genes (SEQ ID NO: 1). Since type-I PKSs multifunctional enzymes have repetitive domains, hybridization between *S. melanosporofaciens* genomic DNA and probe Kp38 gives several signals. The two most intense signals that correspond to the 3.8 and 5.5 BamHI fragments of strain EF-76 were absent from the hybridization pattern of strain FP-60.

Figure 3:
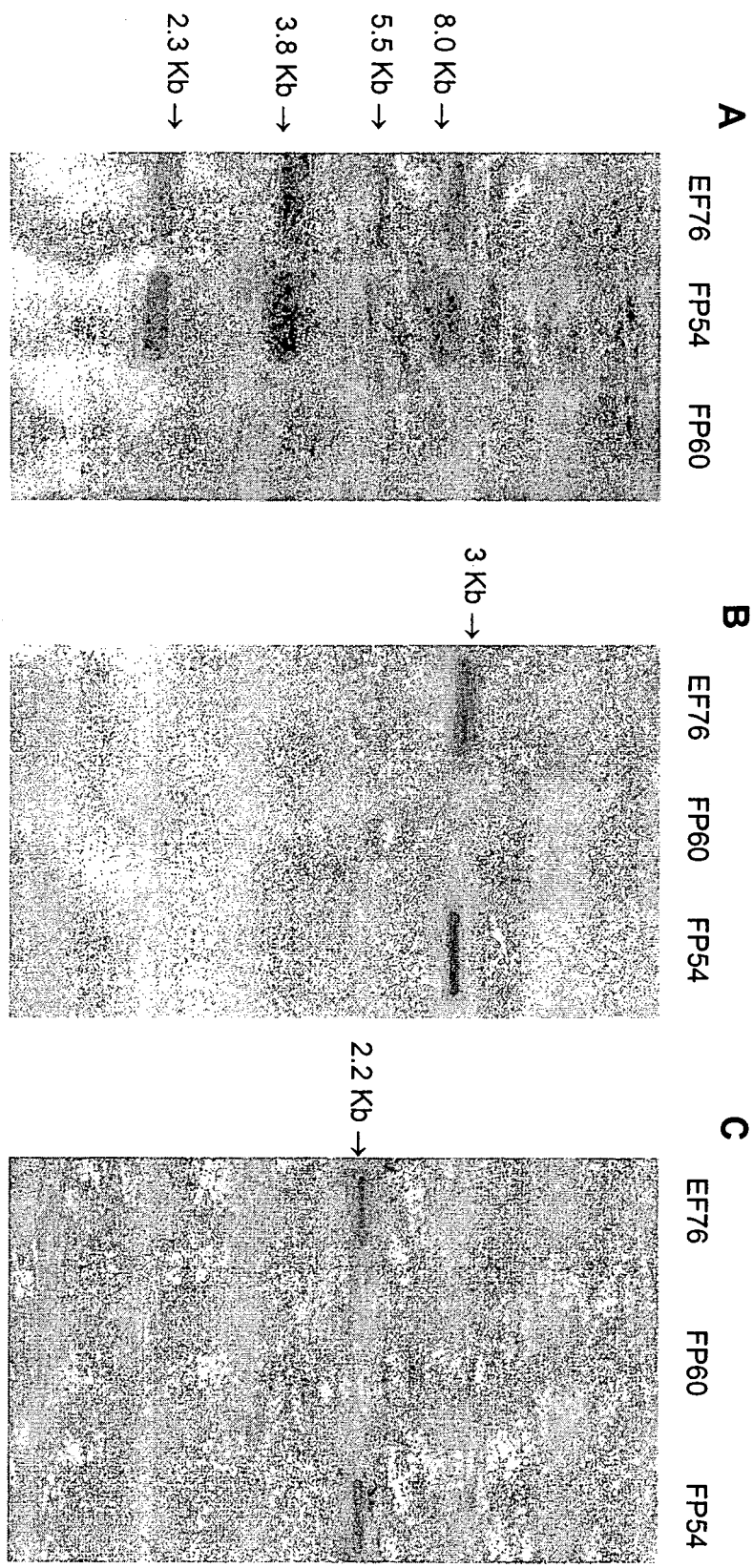
FIG. 3 presents a southern blot hybridization of BamHI-digested genomic DNAs and probes Bm27 (SEQ ID NO: 2) (A), Bm3 (SEQ ID NO: 3) (B), and BS15 (C)

FIG. 3 presents a southern blot hybridization of BamHI-digested genomic DNAs of *S. melanosporofaciens* strains EF-76, FP-54 and FP-60 and probes Bm27 (A), Bm3 (B), and BS15 (C). Probe Bm27 contains a sequence encoding a putative formaldehyde dehydrogenase. Probe Bm3 contains some sequences encoding a putative transporter, a chitosanase, and a glycosyl transferase. Probe BS15 contains some sequences encoding a putative alcohol dehydrogenase and a methyl malonate-semialdehyde dehydrogenase. No modification was detected in the genome of strain FP-54. The hybridization pattern of strain FP-60 with probe Kp38 was different from those of strains EF-76 and FP 54. Strain FP-60 was the only strain displaying no hybridization signal with probes Bm3, Bm27 and BS15.

Example 6

In Vitro Antibiosis Assays

Crossed resistance between EF-76. FP-54 and FP-60

Crossed resistance tests between strain EF-76 and FP-54 and FP-60 strains were carried out as described above except that YME was used instead of TSA and the plates were incubated 48 h following the overlay. Each of the three strains was individually plated on YME and their antagonistic properties against the two other strains were recorded.

FP-60's growth was inhibited in the presence of strains EF-76 and FP-54 (data not shown). Growth of strains FP-54 and EF-76 was not affected by the presence of each other or by the presence of strain FP-60 (data not shown). Since a strain that produces an antibiotic is generally resistant to it and one that is sensitive to this antibiotic does not produce it, these results suggest that FP-60 does not produce geldanamycin while EF-76 and FP-54 do. Antibiosis of EF-76 against *B. cereus* and *S. scabies*

The ability of *S. melanosporofaciens* strains to inhibit the growth of *B. cereus* ATCC 14579 and *S. scabies* EF-35 was tested on YME as follows. *S. melanosporofaciens* strains (108 spores) were streaked in the center of YME plates. The plates were incubated 5 days at 30° C. and then covered with an overlay of soft TSA (0.3% agar) containing *B. cereus* ATCC 14579 or *S. scabies* EF-35 (50011 of an overnight culture in 4 ml of soft TSA). After 24 h at 30° C., the diameter of the antibiosis zones around the *Streptomyces* inoculum was recorded. This experiment was carried out in five replicates. Strain EF-76 was shown to inhibit the growth of *S. scabies*. Antibiosis of FP-54 and FP-60 against *P. fragariae, Bacillus cereus*. and *S. scabies* EF-35

The antagonistic property of the fusants was tested on *Bacillus cereus* ATCC 14579, *Phytophthora* fragariae var. *rubi* 390 and *S. scabies* EF-35. The *Streptomyces* strains, *B. cereus* and *P. fragariae* var. *rubi* were grown on yeast malt extract (YME) broth (4 g L-lyeast extract, 4 g L-1 glucose, 10 g L-1 malt extract, 15 g L-1 agar) or agar (15 g/l) (Pridham et al. 1956-1957), on trypticase soy broth (TSB), and on potato dextrose agar (PDA) (Difco Laboratories, Montreal, Canada), respectively.

The ability of fusants to inhibit the growth of *B. cereus* ATCC 14579 and of *S. scabies* EF-35 was tested on YME plates as follows. *Streptomyces* strains (108 spores) were streaked in the center of YME plates. The plates were incubated 5 days at 30° C. and were then covered with an overlay of soft trypticase soy agar medium (TSA, 0.3% agar) containing *B. cereus* ATCC 14579 or *S. scabies* EF-35 (500 µl of an overnight culture in 4 ml of inoculum soft TSA). After 24 h at 30° C., the diameter of the antibiosis zones around the *Streptomyces* inoculum was recorded. This experiment was carried out in five replicates.

The ability of the fusant strains to inhibit *P. fragariae* var. *rubi* was tested as follows. Fusant strains were streaked (108 spores) in the center of PDA plates and incubated for 2 days at 30° C. A piece of PDA medium (8-mm diameter) from a 7-day-old culture of *P. fragariae* var. *rubi* 390 was then placed 1 cm from the border of the Streptomyces inoculum. *Phytophthora* growth inhibition was recorded after 5-7 days of incubation at 15° C.

Table 1 below shows the growth inhibition achieved by EF-76, FP-54 and FP-60 against certain strains and their retardation factor (Rf), namely the ratio of the compound migration distance on distance traveled by the solvent front. As may be seen in Table 1, strain FP-60 lost the ability to inhibit the growth of *B. cereus* ATCC 14579, *P. fragariae* var. *rubi* 390 and *S. scabies* EF-35 (FIG. 1). Strain FP-54 exhibited higher antagonistic activities, defined herein as the growth inhibition zone, against these three microorganisms than did the wildtype strain EF-76 (FIG. 1). The higher antagonistic property of strain FP-54 might be the consequence of a cumulative effect of various secondary metabolites. Indeed, strain FP-54 was shown to produce, in addition to geldanamycin, two other antimicrobial compounds that were absent in culture supernatants of strain EF-76.

TABLE 1

Antagonistic properties of EF-76 and fusant strains FP-54 and FP-60.

| Strains | Antagonistic properties against *Bacillus cereus, Streptomyces scabies* and *Phytophtora fragariae* var. rubi[a] | Retardation factor (Rf) of products inhibiting the growth of *Bacillus cereus*[a] |
|---|---|---|
| EF-76 | + | 0.51[b], 0.44 |
| FP-54 | ++ | 0.85, 0.72, 0.51[b], 0.44 |
| FP-60 | − | no compound found |

− No growth inhibition, + growth inhibition, ++ higher level of growth inhibition
[a]Compounds were separated by thin layer chromatography on silica gel 60F-250
[b]Rf corresponding to geldanamycin (Toussaint et al. 1997)

Antibiosis of supernatant

Antibiotics were isolated from 96-h-old YME cultures. Culture supernatants (500 ml) were filtered through paper (Osmonics™, Minnetonka, Minn., USA) and the filtrates were extracted three times with one-third volume of chloroform. The chloroform fractions were evaporated on a BüChi Rotavapor R-14™ (Büchi Laboratoriums, Flawil, Switzerland). The resulting material was then dissolved in chloroform and separated by thin-layer chromatography on glass plates precoated with 0.5 mm silica gel 60F-250 using chloroform:methanol (95:5, v/v). After migration, the dried TLC was overlaid with soft TSA containing *B. cereus* ATCC 14579. The TLC plate was then incubated overnight at 30° C. and the presence of growth inhibition zones was recorded.

In addition to geldanamycin, strain FP-54 produced antibiotics that were absent in strain EF-76 supernatant (Table 1).

Strain FP-60 lost the ability to synthesize geldanamycin (Table 1).

This example shows that intraspecific protoplast fusion can be used to modify the biocontrol agent's efficiency of the strains of the present invention.

Example 9

Effect on Potato Scab of Seed Inoculation with Two Fusants of EF-76

The ability of the fusant strains to reduce common scab symptoms was tested both in controlled and field conditions.

Growth Chamber

Inoculum for the growth chamber assay were prepared by growing *S. scabies* EF-35 for 2 weeks at 30° C. in 50-ml tubes containing vermiculite saturated with Say-solution (Faucher et al. 1992). The antagonistic strain EF-76 and the fusant strains FP-54 and FP-60 were grown on YME agar for 10 days at 30° C. Their spores were collected with a glass beads and then mixed with talc (108 spores/g talc). Scab-free potato tubers cv. Green Mountain were planted in 25-cm-diameter pots containing sterile sand and vermiculite (2:1, w/w) mixed with the pathogenic inoculum. At plantation, 0.5 g of talc with or without an actinomycete strain was sprinkled on the top of each tuber. Potatoes were grown at 25° C. with a 16-h photoperiod. Progeny tubers were harvested after 12 weeks and examined visually for common scab symptoms. A disease index (1-10) corresponding to the surface of coverage by common scab lesions was assigned to each infected tuber. On this scale, 1 means no disease while 10 means 100% surface coverage. The experiment was carried out in five replicates.

Field

The field experiment was carried out in a field naturally infested by S. scabies (L'Assomption, Canada). Plots consisting of four rows of 0.5m×4m were planted with 104 potato seeds cv. Shepody. Plots were arranged as a completely randomized block with four replicates. The inoculum to be applied on the tubers was prepared as follows. Strains EF-76, FP-54 and FP-60 were grown in YME supplemented with 10 mM $CaCO_3$ for 7-10 days in a 5-I bioreactor. The cultures were centrifuged and the pellets were freeze-dried for 18 h. Dried biomass (1 g) prepared as described before? was mixed with talc (300 g). Talc containing lyophilized bacteria (dried biomass) (0.5 g) was sprinkled on the top of each tuber at plantation. In control plots, talc without bacteria was applied on potato seeds. At harvest, tubers were examined for common scab symptoms as described above.

Figure 4:
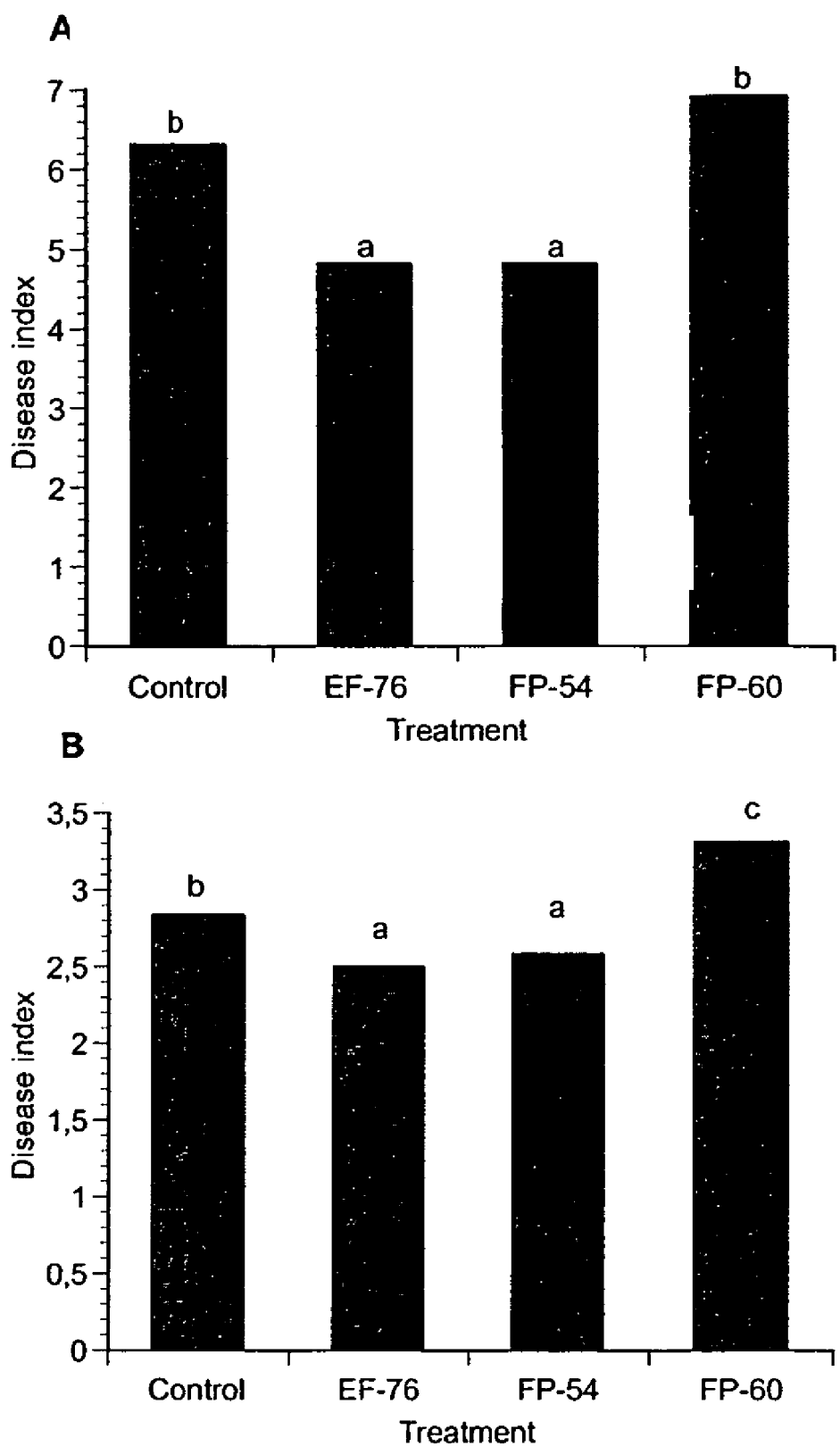
FIG. 4 presents the effect of *S. melanosporofaciens* EF-76 and of two fusant strains on common scab of potato. Panel (A) and B) presents assays in a growth chamber and in the field, respectively. Bars accompanied by the same letter indicate that the corresponding treatments did not significantly differ (p<0.05)*.

S. melanosporofaciens EF-76 had the capacity to reduce common scab both in controlled and field conditions. The disease index was reduced from 6.30 to 4.81 and from 2.83 to 2.49 in growth chamber and field experiments, respectively (FIG. 4). Strain FP-54 also reduced common scab severity on potato tuber, but no significant difference was observed between the disease index attributed to tubers treated with strain EF-76 or with strain FP-54 (FIG. 4).

It was observed that FP-54 strain survived in soil and significantly reduced the common scab disease incidence as compared to the reduction achieved with the control and EF-76. The disease incidence of tubers treated with FP-54 was of 56%, that with those treated with the control was of 72%, and that those treated with EF-76 was of 70%.

Strain FP-60 showed no protective effect against common scab; moreover, the disease index of tubers treated with this recombinant was higher than the index associated with potato tubers from the control treatment (FIG. 4). This suggests that geldanamycin biosynthesis is a mechanism associated with biocontrol. Strain FP-60 is not only ineffective as a biocontrol tool but potatoes treated with this fusant had a disease index higher than potatoes from control treatment.

It also appears that the strains capable of producing geldanamycin, for instance strains EF-76 and FP-54, are effective against the scab causative agent.

It has been shown in Example 5 under subtitle "Genetic characterization of strains FP-54 and FP-60" that EF-76 and FP-54 possess sequences homologous to probes Bm3, Bm27 and BS15 while FP-60 does not. These results therefore suggest that the production of geldanamycin by EF-76 and FP-54 coincides with the presence of each or all sequences homologous to probes Bm3, Bm27 and BS15 in these strains.

Example 6

In Vitro Antibiosis Assays with Other Geldanamycin-Producing Strain

The ability of Streptomyces hygroscopicus var. geldanus ATCC 55256 to inhibit the growth of B. cereus ATCC 14579 and of S. scabies EF-35 was tested on YME plates as follows. Streptomyces strains (108 spores) were streaked in the centre of YME plates. The plates were incubated 5 days at 30° C. and were then covered with an overlay of soft trypticase soy agar medium (TSA, 0.3% agar) containing B. cereus ATCC 14579 or S. scabies EF-35 (500 µl of an overnight culture in 4 ml of inoculum soft TSA). After 24 h at 30° C., the diameter of the antibiosis zones around the Streptomyces hygroscopicus var. geldanus inoculum was recorded. This experiment was carried out in three replicates. The antibiosis capacity of ATCC 5256 was similar to that of EF-76.

It is therefore submitted that geldanamycin-producing strains may be used as biocontrol agents against common scab.

Any probe or primer of at least 12 nucleotides in length derived from Bm3, Bm27, BS15, the amino DHQ synthase and the geldanamycin coding sequence (SEQ ID NO: 7) will be used to screen and select a strain useful as a biocontrol agent against common scab. In the alternative, a ligand to the protein geldanamycin may be used for the same purpose.

Although the present invention has been described hereinabove by way of preferred embodiments thereof, it can be modified, without departing from the spirit and nature of the subject invention as defined in the appended claims.

REFERENCES

Agbessi, S, Beauséjour, J and Beaulieu, C. 2003. Antagonistic Properties of Two Recombinant Strains of Streptomyces melanosporofaciens Obtained by Intraspecific Protoplast Fusion. J. Appl. Microbiol. Biotechnol. 62: 233-238.

Allan C R and Hadwiger L A 1979 The fungicidal effect of chitosan on fungi of varying cell wall composition. Exp. Mycol. 3, 285-287.

Benhamou N and Thériault G 1992 Treatment with chitosan enhancesresistance of tomato plants to the crown and root rot pathogen, Fusarium oxysporum f. sp. radicis-lycopersici.Physiol. Mol. Plant. Pathol. 41, 33-52.

Benhamou N, Lafontaine P J and Nicole M 1994 Induction of systemic resistance to Fusarium crown and root rot in tomato plantsby seed treatment with chitosan. Phytopathology 84, 1432-1444.

Brzezinski R, Boucher I, Dupuy A and Plouffe B 1997 Actinomycetes as model organisms for the study of chitosanases. In ChitinHandbook. Eds. R A A Muzzarelli and M G Peter. pp 291-295.European Chitin Society, Torrette.

Côté N, Hogue R, Beaulieu C and Brzezinski R 2001 Suppressive effect of chitin waste-based composts on common scab of potato. In Chitin Enzymology. Ed. R A A Muzzarelli. pp 155-161. Atec Edizioni, Italy.

Cuero R G, Duffus E, Osuji G and Pettit R 1991 Aflatoxin control in preharvested maize: effects of chitosan and two microbial agents. J. Agric. Sci. 117, 165-169.

DeBoer C, Meulman P A, Wnuk R J and Peterson D H 1970 Geldanamycin, a new antibiotic. J. Antibiotics 23, 442-447.

Doumbou C L, Akimov V and Beaulieu C 1998 Selection and characterization of microorganisms utilizing thaxtomin A, phytotoxin produced by Streptomyces scabies. Appl. Environ. Microbiol. 64, 4313-4316.

Doumbou C L, Akimov W, Côté M, Charest P M, Beaulieu (2001a) Taxonomic study on non pathogenic streptomycetes isolated from common scab lesions on potato tubers. Syst Appl Microbiol 24:451-456.

Doumbou C L, Hamby Salove M K, Crawford D L, and Beaulieu C (2001b) Actinomycetes, promising tools to control plant diseases and to promote plant growth. Phytoprotection 82:85-102

Eckwall E C and Schottel J L 1997 Isolation and characterization of an antibiotic produced by the scab disease-suppressive *Streptomyces* diastatochromogenes strain PonSSII. J. Ind. Microbiol. Biotechnol. 19, 220-225.

Faucher E, Savard T, Beaulieu C (1992) Characterization of actinomycetes isolated from common scab lesions on potato tubers. Can J Plant Pathol 14:197-202

Fujimoto Y, Imamura A, lyeiri C, Shoji S, Kubota Y, Shibata M (1990) Features of regenerated clones with or without fusion treatment between auxotrophic mutants of *Streptomyces antibioticus* and their antibiotic productivity. Agric Biol Chem 54:2855-2861

Fukamizo T and Brzezinski R 1997 Chitosanase from Streptomycessp. strain N174: A comparative review of its structure and function. Biochem. Cell Biol.75, 687-696.

Goyer C, Otrysko B and Beaulieu C 1996 Taxonomic studies on streptomycetes causing potato common scab: A review. Can. J. Plant Pathol. 18, 107-113.

Goyer C, Vachon J and Beaulieu C 1998 Pathogenicity of *Streptomyces scabies* mutants altered in thaxtomin A production. Phytopathology 88, 442-445.

Hayashida S, ChoiMY, Nanri N, Yokoyama M and Uematsu T 1989 Control of potato common scab with an antibiotic biofertilizer produced from swine feces containing *Streptomyces* albidoflavusCH-33. Agric. Biol. Chem. 53, 349-354.

Hirano S and Nagao N 1989 Effects of chitosan, peptic acid, lysosyme and chitinase on the growth of several phytopathogens. Agric. Biol. Chem. 53, 3065-3066.

Hopwood D A, Bibb M J, Chater K F, Keiser T, Bruton C J, Kieser H M, Lydiate D J, Smith C P, Ward J M, Schrempf H (1985) Genetic manipulation of *Streptomyces*: a Laboratory Manual, The John Innes Foundation, Norwich Hopwood D A, Wright H M, Bibb M J (1977) Genetic recombination through protoplast fusion in *Streptomyces*. Nature 168:171-174

Labrie C, Leclerc P, Côté N, Roy S, Brzezinski R, Hogue R and Beaulieu C 2001 Effect of chitin waste-based composts produced by two-phase composting on two oomycete plant pathogens. Plant Soil 235, 27-34.

Liu D, Anderson N A and Kinkel L L 1995a Biological control of potato scab in the field with antagonistic *Streptomyces scabies*. Phytopathology 85, 827-831.

Lorang J M, Liu D, Anderson N A and Schottel J L 1995 Identification of potato scab inducing and suppressive species of *Streptomyces*. Phytopathology 85, 261-268.

Pridham T G, Anderson P, Foley C, Lindenfelser L A, Hessetime C W, Benedict R G (1956-1957) A selection of media for maintenance and taxonomic study of streptomycetes. Antibiot Annu 1956-1957:947-953

Robinson M, Lewis E, Napier E (1981) Occurrence of reiterated DNA sequences in strains of *Streptomyces* produced by an interspecific protoplast fusion. Mol Gen Genet 182:336-340

Rothrock G S, Gottlieb D (1984) Role of antibiosis of *Streptomyces hygroscopicus* var. *geldanus* to *Rhizoctonia solani* in soil. Can J Microbiol 30:1440-1447

Ryan A D and Kinkel L L 1997 Inoculum density and population dynamics of suppressive and pathogenic *Streptomyces* strains and their relationship to bacterial control of potato scab. Biol. Control 10, 180-186.

Savard T, Beaulieu C, Boucher I and Champagne C P 2002 Antimicrobial action of hydrolyzed chitosan against spoilage yeasts and lactic acid bacteria of fermented vegetables. J. Food Protection 65, 828-833.

Toussaint V, Valois D, Dodier M, Faucher E, Déry C, Brzezinski R, Ruest L, Beaulieu C (1997) Characterization of actinomycetes 237 antagonistic to *Phytophthora fragariae* var. *rubi*, the causal agent of raspberry root rot. Phytoprotection 78:43-51

Trejo-Estrada S R, Sepulveds I R and Crawford D L 1998 In vitro ans in vivo antagonism of *Streptomyces* violaceusniger YCED9 against fungal pathogens of turfgrass W J Microbiol Biotechnol 14 :865

Valois D, Fayad K, Barasubiye T, Garon M, Dery C, Brzezinski R, Beaulieu C (1996) Glucanolytic actinomycetes antagonistic to *Phytophthora* fragariae var. *rubi*, the causal agent of raspberry root rot. Appl Environ Microbiol 62:1630-1635

Vruggink H 1970 The effect of chitin amendment on actinomycetes in soil and on the infection of potato tubers by Streptomyce scabies. Neth. J. Plant Pathol. 76, 293-295.

Wang G H 1992 Inhibition and inactivation of five species of foodborne pathogens by chitosan. J. Food Protection 55, 916-919.

---

What is claimed is:

1. A biologically pure culture of the *Streptomyces* strain deposited at the American Type Culture Collection (ATCC) Accession number BAA-668, or a variant thereof that possesses biocontrol efficiency against common scab.

2. A composition comprising an inoculum of a strain as recited in claim 1 and a carrier.

3. The composition as recited in claim 2, wherein the carrier comprises chitosan.

4. The culture as recited in claim 1 which is the *Streptomyces* strain deposited at the American Type Culture Collection (ATCC) Accession number BAA-668.

5. A composition comprising an inoculum of the strain as recited in claim 4 and a carrier.

6. The composition as recited in claim 5, wherein the carrier comprises chitosan.

* * * * *

SEQUENCE LISTING

```
<160> NUMBER OF SEQ ID NOS: 7

<210> SEQ ID NO 1
<211> LENGTH: 2700
<212> TYPE: DNA
<213> ORGANISM: Artificial
<220> FEATURE:
<223> OTHER INFORMATION: probe

<400> SEQUENCE: 1
ggtctcgagg gcccggccgt gaccatcgac accgcctgct cgtcgtcgct ggtggcgctg        60
caccttgccg cgcaggcgct gcggcagggt gaatgctcgc tggcgctggc gggcggggtg       120
gccgtgatgt ccaccccggg caccttcgtg gagttcagcc gtcagcgggg tcttgcgccg       180 gacgccggt gcaaggcgtt cgcggcggca cggacggta cgggctgggg cgagggtgtg        240
ggcatgctgc tgctggagcg gctgtcggac gcgcggcgca acggacacca gatcctcgcg       300
```

-continued

```
gtggtacgcg gctccgccgt caaccaggac ggtgcgagca acgggctcac cgcggcccaa      360
tggccctcgc aacagcgggt gatccgggcg gcgctggcca acgcgcggct gtcggcggcc      420
gaggtggacg tggtcgaggc gcatggtacg ggtaccacgc tgggcgaccc gatcgaggcg      480
caggcgcttc ttgccacgta cggccgtgaa cacaccgacg accagcccct gtggctcggc      540
tcgatcaagt ccaacatcgg gcacacccag gccgcggccg gtgtcgcggg cattatgaag      600
atggtgcttg ccatgcggca tggtctgttg ccgcagacgc tgggcgtcga cgaaccgtcg      660
ccgcacatcg actggacggc gggagcctcg aagctgctca ccgaggccag ggcctggccc      720
gagaccgacc gcccacggcg ggcgggcgtc tcgtccttcg gcctcagcgg caccaacggc      780
cacatcattc tcgaacagga gccgccgacc gaggccgacg aggaaacctc ccaggaggac      840
gcgcaacttc ctcccgccgt cgtgccatgg gtgctgtcgg cgaagtccga tgccggtgtg      900
cgggggcagg ccgcgcgact gcagtcggcg gtggccgggg ataccagccc ggggatgacg      960
gacatcggtc tgtcgctggt caccacgcgt gcggcgttcg agcggcgggc ggtggtactg     1020
ggtggtgacc gtgccgcgct cgtcagtggc ctgaccgcgc tgaccgaggg ccggaggcg      1080 acgcgcgtgg tgcggggggc cgtggtcggc tccgatgccc gagtggcctt tgtctttcct     1140
ggtcgagggg tcgcagtggg tggggatggc ggctgggttg ctggagtctt cgccggtgtt     1200
cgcggagcga ttggtgagtg tgcggcggct tcggcgccgt tcgtcgactg gtcgctcggg     1260
gatgtgttgc ggggtgggaa gggtgctgcg gaggcgttgg agcgggtgga tgtggtgcag     1320
ccggtgttgt gggcggtgat ggtgtcgttg gcggagctgt ggcgttcgta cggtgtggag     1380
cctgcggccg ttatcggtca ttcgcagggt gagatcgcgg cggcgtgtgt ggcgggtgcg     1440
ttgtcgctgg aggacgccgc gcgcgtggtg gcgttgcgaa gccaagcact gcgggcgttg     1500
tccggcggtg gtggcatggt gtcggtatca ctgcccgtga aggcggtacg agagcggctg     1560
gtccggtggg gtgagcggct gtcggtgcag gcggtgaacg ggccctcggc ggttgttgtc     1620
tcgggtgacg cggacgcgtt ggacgagctg ctggcggtgt gcgagggcga ggagatccgg     1680
gcccgtcgca tccccgtgga ctacgcctcg cactgcgccc atgtggagga aatcgaggag     1740
acgttgttgc gggagctggc ggatatcgct ccccgggcgt cgtcggtgcc gttctactcc     1800
agggtcacgg caggcgtgct cgatacgacc ggactggacg ccgggtactg gtaccggaat     1860
ctgcgtcaga cggtccgctt cgatgagacc gtacgcaccc tcctggccga cggcttccag     1920
gtgttcatcg aggccagcgc ccaccccgtc ctgacgatgg gagtggagca gacggccgag     1980
gaccacggca cccgcgtcac cgccgtcggt tccctgcgcc gcgacgatgg cggtcccgac     2040
cggttcgcca cctccctcgc cgaggcgtat gtcggcggcg cgcccgtcga ctgggcgagg     2100
atgttcgccg aacgggcgc ggagcgggcc gatctgccga cgtatgcctt ccagcgcacg     2160
cacttctggc tggagtccga gacggtcgag gccggtgatg tgccgtcggt ggggctggac     2220
tcggccgggc atccgttgct gggtgccgcc gtgccgctgc ccgactccga cggcttcctg     2280
ctcaccggcc ggctgtcgct ccgtacccat ccctgggtcg ccgaccacgc ggtggcggat     2340
gtaacgctgc tgcccgggac ggccttcgtg gagctgctga tgcgggccgg tgacgcggtc     2400
ggctgcgacc gggtggacga actgaccctg ggagcaccgc ttgtgctgcc cgagcagggc     2460
acggtccggc tgcaggtcgc cgtcggcggc cccgacgagg cggggcggcg ctcggtcggt     2520
gtgtacgcgc agacggagga cggccctctgg acgcagcacg cgaccggtgt gctcggcggc     2580
ggtgtgctcg gcggcggcag cagctcggcc gatcgcgtca ctgagacgga ggcatggcca     2640
```

```
ccgactggtg cggaggccgt tgatgtcgcc gggctctacg agaggttcgc ccggaccgga    2700
```

<210> SEQ ID NO 2
<211> LENGTH: 1114
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (611)..(611)
<223> OTHER INFORMATION: n is a, c, g, or t

<400> SEQUENCE: 2

```
tacccgggtg gcgctggcct tcgtcagtng ctatctcttc gggcgcggcc acaggggggac    60 cttggtcctc ggcctcgcgg tctcgccgcg ggcaagcggc tctccggtat cagcccaccg   120
ggcgcccagg cactgaagtc ctccgagctc ggcaagctgg ccaggagat cggcagccgg    180 ctggtctccg cgggtcggga ggcggccatg tcggcggcca gtagccgcat cgacggcctg   240
agcgacccgc tggagcaccg cgccacggcg ctgcgcaccg gcggcgcggg gggcggggag   300
ccggagscgg ggaggacgag gagccggacg agcaggagga gcgcgagcca cgcgagccca   360
ccggcaagca gcagcrcaag ccggccgacc gtncggcgca ggccaggaag cggacggytc   420
cnaagggctc gcgcgacgna gccagangtg agggccatgg ctgaggaaac ccccaagggg   480
cgggccsgtg ggcgcsgcgc ctgcccaccg accacctgnc gaagnaagca cagggcctgc   540
tgatggcgct ggscgaaaag gctctggaat cggtcaccca cctgggggc aaccccggga    600 cgggcgcgct naagggcgga ctggaccagg tcaaggcaa ggtcgtcgac acggccaagg    660
agcagatcaa ggagaaggtc aaggaccagg tcaaggaaaa ggtcgtcgac aaggccaaga   720
gcttcatccc gggcctcggc ggtggcgcg acgtggcgg caaggcggc aagaagctca     780 aggtcaccaa catcgtggag cagatcgacg tgggcgcgcc cctctccctc acctacaacc   840
tctggacgga gtgggagaac ttcccctcgt acatgaagaa ggtcgaggac gtccagaacc   900
agggcgagga ggagggtgag gacgaggacg gghccgggac ggaatccgag tggaaggccc   960
aggtcttctg gtcgcaccgc aagtggcagg cagaggtcgt cgagcaggtg cccgaacaag  1020
scggatcatc tggagcgtct vcgggccgad caagggmcca tgtscgacrg vacgatcacc  1080
```

-continued

```
ttccatgagc tggcccccga gctcacccgg atcc                              1114

<210> SEQ ID NO 3
<211> LENGTH: 1326
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (924)..(924)
<223> OTHER INFORMATION: n is a, c, g, or t

<400> SEQUENCE: 3
gcatgcgsgc gggcggcgaa ssgcgttcgt cggtcacggg ggcgtaggcg taggcccsgc     60
cacgcggggt gcgggtgagc aactgcttgg tgtgcatacg ggtgaggatc gtcaccacgc    120
tgttgtaggc cagttcgccg ccgaggcgtt cggtgacctc ccgggggggtc agcgcgccgt    180 cggcccgctg cagcagttcg aggatctcgg cctcgcgggc accgttgggc cgcttgggcc    240
cgtgtcctgg cgtgcggatg cccatgcggt tggcctccct catctcatca cccbacactc    300
gtgtaggact cctacaccgg tgtaaaagct gttgtctccc aagtgtgcca tgcacgcgtg    360
cctgggcaga actctgcctt gggcgggcac ggscggaaag gaccctgcgg tgcctttggc    420
cctcaacccg ctggatgccg ccgaactgct gacagcgttc ggcacggcgg tgtcttcgt    480 ggtgctgttc gccgagaccg gacttctgat cggcttcttc ctgcccggtg actccctgtt    540
ggtcaccgcc ggcctkctgt gtacggcctc gggcaggggc gtccacctgt cggtgcccgg    600
tgtgccggtc cgtacccgcg gccggcacct gatcgacggt gttaggcgtg cggaggagct    660
tctyggccgv tacgaccgct accggttcct ctgttcgcgc tgatcgacgc gtytycccgc    720
tgccgctcgc cctgggagcg ctcaggtccc gccgggcccg caccgccgsg gagccgaccg    780
tggggagcgc caagtgaaga caccttcccc tgatccacaa cgtgtacgcg atcggcggva    840
cgatccgcac caagctaaat ctcgccgccg ggctcgccga ccggcacrag gtgacgaycg    900
tatcgatgct ccgccaccgc accnaccgc gattccgtca tcgatccacg ggtgacggtc    960
gtgcccctgg ttgacataca cgcggacgcc gccgacccc tgctgcatca gccggccgag   1020
gtcttcccca ccgccgagaa gcggtacagg cagtacagcc gcctcaccga ccagggggcg   1080
cgcgagtacc tgcggaagct gcgacgcgga cgtgatcatc ggcacgcggc cgggcatcaa   1140
tgtgtacctg gccccttcgc accgcccgg gcactgcgca tcgcccagga acacctcacc   1200
cacgasacgc acaccaagag ctgcgcgccc agctcgsssg ccagtaccgc gacctggatg   1260
ccgtggtcac cacgaccgaa gccgacgcgg ccgtctaccg ggcgagatgc ggctgccggg   1320
cggggg                                                             1326

<210> SEQ ID NO 4
<211> LENGTH: 354
<212> TYPE: PRT
<213> ORGANISM: Streptomyces hygroscopicus

<400> SEQUENCE: 4

Met Thr Thr Ser Thr Ser Ser Pro Ala Ala Ser Ser Ala Ser Pro Ala
1               5                   10                  15

Arg Gln Val Val Val Gly Leu Ala Glu Arg Ser Tyr Thr Val His Ile
            20                  25                  30

Gly His Gly Val Gln Arg Leu Leu Pro Gln Val Val Ala Ala Leu Gly
        35                  40                  45
```

-continued

```
Ala Arg Arg Ala Val Val Thr Ala Arg Pro Ala Glu Gln Thr Pro
     50                  55                  60

Asp Pro Gly Val Pro Ser Leu Val Pro Ala Arg Asp Gly Glu Ala
 65                  70                  75                  80

Ala Lys Asp Leu Ala Ala Val Thr Asp Leu Cys Arg Arg Phe Val Gly
                 85                  90                  95

Phe Gly Leu Thr Arg Ser Asp Val Val Ser Cys Gly Gly Thr
            100                 105                 110

Thr Thr Asp Thr Val Gly Leu Ala Ala Ala Leu Tyr His Arg Gly Thr
            115                 120                 125

Pro Val Val His Val Pro Thr Ser Leu Leu Ala Gln Val Asp Ala Ser
            130                 135                 140

Val Gly Gly Lys Thr Ala Val Asn Leu Pro Glu Gly Lys Asn Leu Val
145                 150                 155                 160

Gly Ala Tyr Trp Gln Pro Ala Val Leu Cys Asp Leu Glu His Leu
                165                 170                 175

Lys Thr Leu Pro Glu Arg Glu Trp Arg Asn Gly Leu Gly Glu Ile Ala
            180                 185                 190

Arg Cys His Phe Ile Gly Ala Pro Asp Leu Asp Gly Leu Pro Leu Leu
        195                 200                 205

Asp Gln Ile Ser Ala Ser Val Thr Leu Lys Ala Gly Ile Val Ala Ala
    210                 215                 220

Asp Glu Arg Asp Ser Gly Leu Arg His Leu Leu Asn Tyr Gly His Thr
225                 230                 235                 240

Leu Gly His Ala Leu Glu Arg Ala Thr Gly Phe Ala Leu Arg His Gly
                245                 250                 255

Glu Gly Val Ala Ile Gly Thr Val Phe Ala Gly Arg Leu Ala Gly Ala
            260                 265                 270

Leu Gly Arg Ile Gly Pro Glu Arg Val Ala Glu His His Asp Val Val
        275                 280                 285

Ala Arg Tyr Gly Leu Pro Thr Ala Leu Pro Pro His Val Ser Val Ser
    290                 295                 300

Glu Leu Val Glu Leu Met Arg Leu Asp Lys Lys Ala Thr Asp Gly Leu
305                 310                 315                 320

Thr Phe Val Leu Asp Ser Pro Ala Gly Pro Gly Leu Val Arg Gly Ile
                325                 330                 335

Ala Glu Asp Thr Val Gly Ala Thr Leu Ala Ala Met Pro Arg Ala Pro
            340                 345                 350

Ala Trp
```

<210> SEQ ID NO 5
<211> LENGTH: 1064
<212> TYPE: DNA
<213> ORGANISM: Streptomyces hygroscopicus

<400> SEQUENCE: 5

```
caccatgcgg gcgcgcgggg catcgccgcg agggtggcgc cgacggtgtc ctcggcgatc     60
ccgcgcacca gtccgggccc cgcggggcta tccaggacga acgtcagccc gtcggtggcc    120
ttcttgtcca ggcgcatcag ctccaccagc tcggacacgg agacatgcgg gggcagcgcg    180
gtcggcaggc cgtagcgggc gaccacgtca tgatgctcgg ccacgcgctc cgggccgatg    240
cgccccagcg cgccggcgag ccggccggcg aaaaccgtgc cgatggccac tccctccccg    300
tgccgcagcg cgaacccggt ggcacgttcc agcgcatgcc ccaacgtgtg tccgtagttg    360
```

```
aggaggtggc gcaggcccga gtcgcgctcg tccgcggcga cgatgcccgc cttgagcgtc    420
acactggccg agatctggtc gagcagcggc agcccgtcga gatcgggcgc gccgatgaag    480
tggcagcggg cgatctcacc gaggccgttg cgccattccc gttcgggcag ggtcttcaga    540
tgttcgaggt cgcagagcac ggccgcgggc tgccagtagg cgccgaccag attcttgccc    600
tcgggcagat tcaccgcggt cttcccgccg acgctcgcgt ccacctgggc gagcagcgag    660
gtcggcacgt gtacgaccgg ggtgccccgg tggtagaggg cggcggccag gcccaccgtg    720
tcggtcgtgg tgccgccgcc acaggacacc accacatccg agcgggtcag tccgaatccg    780
acgaaccggc ggcacagatc ggtcacggcg gccaggtcct tggccgcctc cccgtcgcgg    840
gcgggtacga cgagcgaggg cactcctggg tcgggggtct gctcggcggg ccgcgcggtg    900
accaccaccg ccctgcgcgc gcccagggcg gccaccacct gtgggagcag ccgctgcaca    960
ccgtgtccga tgtgcacggt gtaggagcgt tcggccagcc cgacgacgac ctgtcgggcg   1020
ggggaagcgg aactggcggc cggactggaa gtcgacgtgg tcaa                    1064
```

<210> SEQ ID NO 6
<211> LENGTH: 300
<212> TYPE: PRT
<213> ORGANISM: Streptomyces hygroscopicus

<400> SEQUENCE: 6

```
Met Asp Lys Arg Thr Met Gly Arg His Arg Arg Ile Thr Gln Pro Pro
1               5                   10                  15

Arg Thr Thr Leu Ala Thr Arg Ala Val Leu Ala Ala Gly Val Leu Val
            20                  25                  30

Pro Thr Ile Ala Ser Ala Gly Ser Ala His Ala Ala Thr Pro Gln Ala
        35                  40                  45

Ala Ile Cys Thr Ser Asp Arg Pro Glu Leu Ala Asp Lys Leu Ser Glu
    50                  55                  60

Asp Ile Asn Ser Ala Leu Glu Gly Ser Ala Ala Thr Thr Ala Ile Ser
65                  70                  75                  80

Leu His Asp Arg Thr Thr Asn Thr Thr Cys Thr Leu Asp Ala Asp Arg
                85                  90                  95

His Phe Asp Ser Ala Ser Thr Val Lys Val Thr Val Leu Ser Thr Leu
            100                 105                 110

Leu Trp Asp Ala Gln Lys Asp Asn Arg Ala Leu Thr Gln Glu Glu Lys
        115                 120                 125

Asp His Ala Thr Ala Met Ile Thr Glu Ser Asp Asn Asp Ala Thr Thr
    130                 135                 140

Ala Leu Trp Lys Gln Leu Gly Ala Asp Lys Ile Asn Gly Phe Leu Gln
145                 150                 155                 160

Ala Ala Gly Met Thr Asn Thr Thr Leu Asp Ser Glu Gly His Trp Gly
                165                 170                 175

Leu Thr Gln Ile Thr Ala Asn Asp Glu Glu Lys Leu Leu Gln Leu Val
            180                 185                 190

Thr His Thr Asn Pro Val Leu Ser Asp Asp Ser Arg Ala Tyr Ile Leu
        195                 200                 205

Lys Leu Thr Ala Glu Val Ile Pro Ser Gln Arg Trp Gly Thr Pro Ala
    210                 215                 220

Gly Ala Pro Ser Asp Ala Gln Val His Val Lys Asn Gly Trp Leu Glu
225                 230                 235                 240

Arg Ala Thr Asn Gly Trp Arg Val His Ser Leu Gly Ala Phe Thr Gly
```

```
                    245                 250                 255
Gly Asp His Asp Tyr Thr Ile Thr Val Leu Ser Gln Asp Asn Ala Thr
            260                 265                 270

Met Asp Asp Gly Ile Ala Asn Ile Glu Gly Ile Ala Arg Ala Val His
        275                 280                 285

Glu Asn Leu Asn Ala Pro Val Ser Ser Ala Gln Ser
    290                 295                 300

<210> SEQ ID NO 7
<211> LENGTH: 903
<212> TYPE: DNA
<213> ORGANISM: Streptomyces hygroscopicus

<400> SEQUENCE: 7
ttacgactga gcgctggaca cgggcgcgtt gaggttctcg tggaccgcgc gggcgatgcc      60
ctcgatgttg gcgatgccgt cgtccatcgt ggcgttgtcc tgcgagagca ccgtgatcgt     120
gtagtcgtgg tcgccgccgg tgaaggcgcc gaggctgtgc acccgccagc cgttcgtggc     180
ccgctccagc cagccgttct tcacatgcac ctgggcgtcg ctcggcgcgc cggccggggt     240
gccccagcgc tgcgagggga tgacctcggc cgtcagcttc aggatgtagg cgcgggagtc     300
atcgctgagc accgggttgg tgtgggtcac cagttggagg agcttttcct catcgttcgc     360
ggtgatctgg gtgagccccc agtggccctc gctgtcgagg gtggtgttgg tcattcccgc     420
ggcctgcagg aacccgttga tcttgtccgc cccgagctgc ttccacagcg cggtggtggc     480
gtcgttgtcg gactctgtga tcatggcggt ggcatggtcc ttctcctcct gtgtcagggc     540
gcgattgtcc ttctgcgcgt cccacagcag ggtgctgagc acggtcacct tgaccgtgct     600
cgcggagtcg aagtgccggt ccgcatccag agtgcaggtg gtgttcgtgg tgcggtcgtg     660
gaggctgatc gccgtggtgg cggcggagcc ctccagcgcc gaattgatgt cctcggagag     720
cttgtcggcg agttccggcc ggtccgaggt gcagatcgcc gcctgcgggg tggccgcgtg     780
agccgacccc gccgaggcga tcgtcggcac gagcaccccg gcggccagca ccgctcttgt     840
cgccagggtg gtacggggag gctgggttat tcgtcggtgt cgacccatgg tgcgcttgtc     900
cat                                                                   903
```